United States Patent [19]
Wheelock

[11] Patent Number: 6,127,136
[45] Date of Patent: Oct. 3, 2000

[54] DETECTION OF DIOXIN-LIKE COMPOUNDS BY DETECTION OF TRANSFORMED AH RECEPTOR/ARNT COMPLEX

[75] Inventor: Geoffrey D. Wheelock, Ithaca, N.Y.

[73] Assignee: Paracelsian, Inc., Ithaca, N.Y.

[21] Appl. No.: 08/601,645

[22] Filed: Feb. 14, 1996

Related U.S. Application Data

[63] Continuation-in-part of application No. 08/546,613, Oct. 23, 1995, abandoned.

[51] Int. Cl.$^7$ .................. G01N 33/548; G01N 33/567
[52] U.S. Cl. .................. 435/7.94; 435/7.21; 436/503; 436/519; 436/530; 436/815
[58] Field of Search .................. 435/7.93, 7.21, 435/7.94; 436/519, 815, 503, 530

[56] References Cited

U.S. PATENT DOCUMENTS

| | | | |
|---|---|---|---|
| 4,238,472 | 12/1980 | Albro et al. | 436/540 |
| 4,798,807 | 1/1989 | Vanderlaan et al. | 530/388.9 |
| 4,891,322 | 1/1990 | Blackburn et al. | 436/64 |
| 4,904,595 | 2/1990 | Gierthy | 435/240.2 |
| 5,378,822 | 1/1995 | Bradfield et al. | 536/23.5 |
| 5,529,899 | 6/1996 | Wheelock et al. | 435/6 |

OTHER PUBLICATIONS

Clement, R.E., Ultractrace dioxin and dibenzofuran analysis: 30 year of advances, Analytical Chemistry 63:1130–1137, 1991.
Vanderlann, M. Et al, Improvement and application of an immunoassay for screening environmental samples for dioxin contamination, Enviro. Toxicol. Chem. 7:859–870, 1988.
Bradfield, C.A. et al, A Competitive binding assay for 2,3,7,8–tetrachlorodibenzo–p–dioxin and related ligands of the Ah receptor, Mol. Pharmacol. 34:682–688, 1988.
Tillitt, D.E. et al, Characterization of the H4IIE rat hepatoma cell bioassay as a tool for assessing toxic potency of planar halogenated hydrocarbons (PHHs) in environmental samples, Environmental Science and Technology 25:87–92, 1991.
Postlind, H. et al, Response of human CYP1–luceferase plastids to 2,3,7,8–tetrachlorodibenzo–p–dioxin and polycyclic aromatic hydrocarbons, Toxicol. Appl. Pharmacol. 118:255–262, 1993.
Denison, M.S. et al, Protein–DNA interactions at recognition sites for the dioxin–Ah receptor complex, Jnl. Of Biological Chem. 264:16478–16482, 1989.
Landers, G.P. et al, Review Article—The Ah Receptor and the Mechanism of Dioxin Toxicity, Biochem. J., vol. 26, pp. 273–287, 1991.
Safe, S., Polychlorinated Biphenyls (PCBs), Dibenzo–Dioxins (PCDDs), Dibenzofurans (PCDFs), and Related Compounds: Environmental and Mechanistic Considerations Which Support the Development of Toxic Equivalency Factors (TEFs), Toxicology, vol. 21, pp 51–87, 1990.

Henry, E.C. et al, Characterization of Multiple Forms of the Ah receptor: Comparison of Species and Bissues, Biochem, 28:6430–40, 1989.
Nebert, D.W. et al, Minireview—Regulation of the Mammalian Cytochrome Pl–450 (CYP1A1)Gene, Int. J. Biochem, vol. 21, No. 3, p 243–252, 1989.
Hoffman, E.C. et al, Cloning of a factor required for activity of the Ah (dioxin) receptor, Science 252:954–958, 1991.
Waithe et al, Biochem & Pharm., 35, pp 2069–2072, 1986.
Pollenz, R.S. et al, The aryl hydrocarbon receptor and aryl hydrocarbon receptor nuclear translator protein show distance subcellular localizations in Hepa 1c1c7 cells by immunofluoresence microscopy, Mol. Pharmacol. 45: 428–438, 1994.
Kanonaga J.E. et al, Affinity purification of sequence–specific DNA binding proteins, PNAS 83:5889–5893.
Chan, W. et al, Baculovirus expression of the Ah receptor and Ah receptor nuclear translocater. Evidence for additional dioxin responsive element–binding species and factors required for signaling, J. Biol. Chem. 269:26464–26472, 1994.
Poland, A. Et al, Characterization of polyclonal antibodies to the Ah receptor prepared by immunization with a synthetic peptide hapten, Molec. Pharmocal. 39:20–26, 1991.
Analytical News (Sep./Oct. 1992).
Vanderlaan, M. Et al, ES&T Critical Review—Environmental Monitoring by Immunoassay, Environ. Sci. Technol., vol. 22, No. 3, pp 247–254, 1988.
Stantostefano, MM. et al, Effects of Ligand Structure on the In Vitro Transformation of the Rat Cytosolic Aryl Hydrocarbon Receptor, Archives of Bioch. And Biophysics, vol. 297, No. 1, pp 73–79, 1992.
Willey, J.C. et al, Acute effects of 12–0–tetradecanoylphorbol–13–acetate, teleocidin B, or 2,3,7,8–tetrachlorodibenzo–p–dioxin on Cultured Normal Human Bronchial Epithelial Cells, Carcinogenesis, vol. 5, No. 2, pp 209–215, 1984.

(List continued on next page.)

*Primary Examiner*—Mary E. Ceperley
*Attorney, Agent, or Firm*—Brown, Pinnisi & Michaels, PC

[57] ABSTRACT

A method of detecting dioxin-like compounds consisting essentially of the group of compounds: polychlorinated dibenzodioxins, polychlorinated dibenzofurans, polychlorinated biphenyls, and structural analogues thereof which exhibit biological activity characteristic of polychlorinated dibenzodioxins, polychlorinated dibenzofurans, polychlorinated biphenyls. The assay includes: 1) an inactive Ah receptor in a form capable of binding to the dioxin-like compounds and being transformed to an active form that forms a complex with ARNT and binds a dioxin responsive element, and 2) a quantity of ARNT sufficient to optimize Ah receptor transformation. A test sample is contacted with the assay under conditions effective to bind the dioxin-like compounds to the Ah receptor and allow transformation of the Ah receptor to an active form that forms a complex with ARNT. The presence of the complex containing the transformed Ah receptor and the ARNT is detected. The presence of the complex containing the transformed Ah receptor and the ARNT is detected with an antibody with a region capable of binding to the ARNT when associated with the complex.

14 Claims, 5 Drawing Sheets

OTHER PUBLICATIONS

Safe, S. Et al., Development and Validation of In Vitro Induction Assays for Toxic Halogenated Aromatic Mixtures: A Review, Toxicology and Industrial Health, vol. 5, pp. 757–775, 1989.

Collins, S. Et al, Carcinogen–Binding Proteins—High–affinity Binding Sites for BenzO[a]pyrene in Mouse Liver Distinct from the Ah Receptor, Molecular Pharmacology, 26:353–359, 1984.

Steinberg, K. et al, Assessment of 2,3,7,8–Tetrachlorodibenzo–p–dioxin Exposure Using a Modified S–Glucaric Acid Assay, Jnl. Of Toxicology and Environmental Health, 16:743–752, 1985.

Waithe et al, Biochem. & Pharm., 41, pp 85–92, 1991.

Zacharewski, T. et al, Application of the in vitro Aryl Hydrocarbon Hydroxylase Induction Assay for Determining 2,3,7,8–Tetrachlorodibenzo–p–Dioxin Equivalents: Pyrolyzed Brominated Flame Retardants, Toxicology, vol. 51, pp 177–189, 1988.

Kramer et al, 2,3,7,8–Tetrachlorodibenzo–p–doxin (TCDD)_Antibody Production and Protein Kinase Activity in Murine B Cells, Biochem and Biophysical Res. Comm., 145(1), pp 25–33, 1987.

Ma, et al, Protein Tyrosine Phosphorylation as an Indicator of 2,3,7,8–Tetrachlorodibenzo–p–dioxin Exposure In Vivo and In Vitro, Biochem. And Biophysical Res. Comm., 189(1), pp. 59–65, 1992.

Rijksen, G. et al, A Nonradioactive Dot–Blot Assay for Protein Tyrosine Kinase Activity, Analytical Biochem. 182:98–102, 1989.

Bombick D.W. et al, 2,3,7,8–Tetrachlorodibenzo–p–dioxin Causes Increases in Expression of Small c–erb–A and Levels of Protein–Tyrosine Kinases in Selected Tissues of Responsive Mouse Strains, Proc. Natl. Acad. Sci. USA, 85:4128–4132, 1988.

Bombick D.W. et al, TCDD (2,3,7,8–Tetrachlorodibenzo–p––dioxin) Causes an Increase in Protein Tyrosine Kinase Activities at an Early State of Poisoning In Vivo in Rat Hepatocyte Membranes, Live Sciences, 41:429–436, 1987.

Clark, G.C. et al, 2,3,7,8–Tetrachlorodibenzo–p–dioxin Stimulation of Tyrosine Phosphorylation in B–lymphosytes: Potential Role in Immunosuppression, Molecular Pharmacology, 39:495–501, 1991.

Freedman, H.J. et al, Aryl Hydrocarbon Hydroxylase in a Stable Human B–lymphocyte Cell Line RPMI–188, Cultured in the Absence of Mitogens, Cancer Research, 39:4605–4611, 1979.

Frechon, D. Et al, Fur (ferric uptake regulation) protein interaction with target DNA: comparison of gel retardation, footprinting and electron microscopy analyses, Biochem—Biophys Res. Commun, 1994, 201:346–355 (Abstr.

Gopal, V. Et al, A point mutation at the junction of demean 2.3/2.4 of transcription factor sigma 70 AB fogales productive transcription and restores its expected mobility on a denaturing gel, Jnl. Mol. Biology, 1994, 242:9–22 (Abstr.

Mezger, V. Et al, Detection of heat shock element–binding activities by gel shift assay during mouse preimplantation development, Dev. Biology, 1994, 165: 627–638 (Abstract).

Stevens, S. Et al, Application of the gel shift assay to study the affinity and specificity of anti–DNA auto–antibodies, Jnl. Immunol. Methods, 1994, 177: 185–190 (Abstract).

Berger, R. Et al, Nonradioactive gel mobility shift assay using chemiluminescent detection, Biotechniques, 1993. 15:650–652 (Abstract).

Hassanain, HH, et al, Enhanced gel mobility shift assay for DNA–binding factors, Anal. Biochem. 1993, 213: 162–167 (Abstract).

Wiland, E. Et al, Binding of low mobility group proteins with DNA examined in homologous and heterologous systems by gel retardation assay, Cell Biol. Int., 1993: 17: 45–53 (Abstract).

Maueler, W. Et al, A gel retardation assay system for studying protein binding to simple repetitive DNA sequences, Electrophoresis, 1992, 13: 7–10 (Abstract).

Qzyhar, A. Et al, High–resolution gel filtration of the ecdysteroid receptor–DNA complex—an alternative to the electropheretic mobility shift assay, J. Chromatogr, 1991, 587:11–17.

Fujiwara, Y et al, Detection of proteins that recognize platinum–modified DNA using gel mobility shift assay, Jpn J. Cancer Research, 1990, 81: 1210–1213 (Abstract).

Brian, At et al, Detection of enhancer binding proteins recognizing the human immunodeficiency virus long terminal repeat by in situ gel retardation, Biochem. Biophys Res. Commun, 1989, 160:268–275 (Abstract).

Sarfert, E et al, DNA binding protein from Strepromyces hygroscopious detection of binding by gel retardation, sedimentation and effects on the transcriptional activity in vitro, Biomed Biochem Acta, 1989, 48:633–643 (Abstract.

Gubler and Abarzua, Nonradioactiv Assay for Sequence–Specific DNA Binding Proteins, BioTechniques, 1995, vol. 18, No. 6, pp. 1008–1013.

DETECTION OF DIOXIN-LIKE COMPOUNDS BY DETECTION OF TRANSFORMED AH RECEPTOR/ARNT COMPLEX

This is a continuation-in-part application of co-pending application Ser. No. 08/546,613, filed Oct. 23, 1995, now abandoned.

FIELD OF THE INVENTION

The present invention is directed to the detection of transformed Ah receptor and the consequent indirect detection of dioxin-like compounds by detection of transformed Ah receptor.

BACKGROUND OF THE INVENTION

Dioxins or dioxin-like compounds are environmental pollutants produced as unwanted byproducts of common industrial processes such as paper bleaching, incineration and chemical manufacturing. Dioxin-like compounds often occur as poorly defined mixtures of these compounds in a larger matrix of other materials that make their analysis and quantitation difficult. There is considerable interest in the study, detection, monitoring and bioremediation of the compounds due to their environmental persistence, extreme chemical stability and extreme multiple toxicities to many organisms.

Dioxins or dioxin-like compounds are a loosely defined family of organochlorine molecules with close structural and chemical similarities. Additionally, these compounds, by virtue of their similar structure and chemistry, share a common mechanism of toxicity. The prototypical dioxin, and the best studied, is 2,3,7,8 tetrachlorodibenzo-p-dioxin (sometimes called 2,3,7,8-TCDD or TCDD or dioxin). Besides 2,3,7,8 tetrachlorodibenzo-p-dioxin, this group of compounds include not only the dibenzo-p-dioxins, but also dibenzofurans, azobenzenes, dibenzo-ethers, certain polychlorinated biphenyls, certain polyaromatics and other compounds. Toxicity of these compounds is dependent on a planar, polyaromatic structure with lateral halogen substitutions.

The biochemical and physiological basis of dioxin toxicity has been the subject of intense scientific scrutiny. Animals vary in their susceptibility to dioxins and in their symptoms. In guinea pigs, as little as 600 ng per kg produces a lethal wasting syndrome. In humans, toxic responses to dioxin exposure include several proliferative aberrations such as hyperkerotinosis and hyperplasia. Despite much research in the area, the biochemical and physiological events that produce toxicity are poorly understood.

Although the ultimate physiological events that produce toxicity are poorly understood, it is generally agreed that toxicity of these chemically and structurally related dioxin-like compounds is due to their ability, by virtue of their chemical and structural properties, to bind to the intracellular Aryl-Hydrocarbon (Ah) receptor. Although the ability of a compound to be a ligand of the Ah receptor is a requirement for dioxin-like toxicity, these compounds must also be able to promote transformation of the receptor to a DNA-binding form subsequent to ligand binding in order to be toxic. The transformation of the Ah receptor comprises a series of poorly understood events that include dissociation of the inactive receptor from a complex of proteins that include one or more molecules of the chaperonin HSP90, the formation of a new complex that includes HSP90-dissociated Ah receptor plus bound dioxin and the nuclear protein ARNT, and the binding of the Ah receptor/ARNT complex to specific DNA sequences.

These sequences, called Dioxin-Response Elements (DREs) or Xenobiotic-Response Elements (XREs), lie upstream of the promoter regions of certain genes, the most studied being the P4501AI gene. The binding of the transformed Ah receptor and associated protein(s) to the DREs enhance transcription of the associated genes. The inappropriate expression of these genes are thought to be the early events in the pleiotropic toxic response to dioxins. Alternatively, dissociation of the Ah receptor from the HSP90 complex, caused by the binding of a dioxin, may free a bound kinase and initiate important intracellular protein phosphorylation events that derange cell homeostasis which manifests as toxicity. In either hypothesis, it is fundamental that dioxins, in order to be toxic, must be able to both bind to the Ah receptor and transform it into an active form, and that this binding/transformation couplet is the central and only defined biochemical event in the pleiotropic toxic effects of dioxins.

Different dioxin-like compounds, although they share a common mechanism of toxicity, have different toxic potencies that can differ by several orders of magnitude. The toxicity of an unknown mixture of dioxin-like compounds can vary considerably depending on the identity and concentrations of the congeners present. Thus, the concept of Toxic Equivalency Factors (TEFs) and Toxic Equivalence (TEQs) have been advanced by some scientists. TEFs are the fractional toxicity of a dioxin-like compounds compared to the most toxic, prototypical 2,3,7,8-TCDD. Published TEFs are arbitrarily assigned values based on consensus toxicities in the scientific literature. TEQs are the estimated toxic potential of a mixture of these compounds calculated by adding their respective TEFs with adjustment for their respective concentrations. TEFs and TEQs have been promoted by the EPA in order to facilitate their risk and hazard assessment of these compounds when they occur as mixtures.

Dioxin-like compounds are commonly detected by extraction from the matrix, which can be a solid, fluid or gas, followed by several chromatographic clean-up steps to remove interfering compounds, and assayed by physico-chemical means, such as gas chromatography and mass spectrometry. The quantified dioxins are then converted to a TEQ by a mathematical formula which relies on the assigned TEFs of the detected congeners and their determined concentrations. To simultaneously measure the seventeen toxic congeners of dibenzo-p-dioxin and dibenzofuran alone by these methods is extremely challenging, is time-consuming and expensive and requires delicate instrumentation and highly trained personnel. (Clement, R. E. Ultratrace dioxin and dibenzofuran analysis: 30 years of advances. Analytical Chemistry 63:1130–1137, 1991).

The difficulty in determining all seventeen toxic dioxin and furan congeners of dioxin have led to several innovations in the detection of these compounds. Detection of dioxin by competitive immunoassay operates as any other competitive immunoassay for small molecules (Vanderlann, M., Stanker, L. H. and Watkins, B. E. Improvement and application of an immunoassay for screening environmental samples for dioxin contamination. Environ.Toxicol.Chem. 7:859–870, 1988). For immunoassays, high specificity for the target molecule is required in order to reduce quantitation errors. However, in this application a specific immunoassay for dioxin would not detect the other toxic congeners. If an immunoassay for dioxin could be purposefully constructed to nonspecifically detect all the toxic congeners of dioxin without detecting the non-toxic ones, there would still be no ability to distinguish the relative toxicity of the mixture detected.

Utilization of ability of the Ah receptor to bind dioxin has been used to construct a competitive binding assay where TCDD is presented to a mixture of mouse cytosol containing HSP90-complexed Ah receptor and a radiolabled dioxin analogue (Bradfield, C. A. and Poland, A. A competitive binding assay for 2,3,7,8-tetrachlorodibenzo-p-dioxin and related ligands of the Ah receptor. Mol.Pharmacol. 34:682–688, 1988). After a period of incubation where unknown dioxin and radiolabled dioxin analogue compete for a limited number of Ah receptor binding sites, the unbound radiolabled dioxin analogue is precipitated and the bound radioactivity counted. The number of counts is inversely proportional to the amount of TCDD present in the sample. The assay requires that the Ah receptor is maintained in a state where it can bind TCDD but not transform. The authors suggest the assay could be used to screen for other ligands of the Ah receptor but do not teach its use to estimate TEFs or TEQs. Indeed, the correlation between TEFs and receptor binding alone is poor and antagonists of the Ah receptor are known which are not toxic since they bind to the receptor but do not transform it.

Bioassays have been constructed to estimate TEQs of complex mixtures that rely on the known correlation between toxicity of a dioxin congener and it's ability to induce P4501AI enzyme activity (Tillitt, D. E., Giesy, J. P. and Ankley, G. T. Characterization of the H4IIE rat hepatoma cell bioassay as a tool for assessing toxic potency of planar halogenated hydrocarbons (PHHs) in environmental samples. Environmental Science and Technology 25:87–92, 1991). These assays require the maintenance of a cell culture which is presented with the test mixture. After an appropriate waiting period the P4501AI is extracted from the cells and its enzymatic activity measured by well known techniques. Recently, assays that use a more active and more easily measured enzyme (luciferase) have been reported (Postlind, H., Vu, T. P., Tukey, R. H. and Quattrochi, L. C. Response of human CYP1-luceferase plasmids to 2,3,7,8-tetrachlorodibenzo-p-dioxin and polycyclic aromatic hydrocarbons. Toxicol.Appl.Pharmacol. 118:255–262, 1993). In these assays an artificial DNA construct containing the promoter region of P4501AI attached to firefly luciferase are introduced into a cell line. In a similar manner, test mixture is presented to the cells and after a waiting period, the luciferase enzyme activity is measured.

The gel mobility shift assay, also called the gel retardation assay or gel shift assay, which detects the change in mobility of DNA when it interacts with protein(s), is the preferred method among scientists to detect transformation of the Ah receptor for research purposes (Denison, M. S., Fisher, J. M. and Whitlock, J. P., Jr. Protein-DNA interactions at recognition sites for the dioxin-Ah receptor complex. Journal of Biological Chemistry 264:16478–16482, 1989). In this method DREs are radiolabled, incubated with a mixture containing transformed receptor, and resolved by non-denaturing gel electrophoresis. The radiolabled DRE bands are then detected by autoradiography. The gel shift mobility assay and its sister technique, DNA footprinting, are widely used in molecular biology to study DNA-protein interactions. In gel mobility shift assays the DNA is the detected species, so they do not identify the bound protein and the identity of the bound protein can only be inferred. The single detection species in the assay prohibits the assays use when other bound proteins co-migrate with the protein of interest. Also, the assay cannot be used if the DNA-protein complex is unstable under the electrophoresis conditions. Gel chromatography has been proposed as substitution for gel electrophoresis to resolve the protein/DNA complex when the DNA-protein complex is unstable under the electrophoresis conditions, the DNA remains the detected species. Rather than curing the deficiencies of the gel shift assay, gel chromatography of the DNA/protein complex exacerbates two problems with gel shift assays. The resolution of gel electrophoresis is excellent, while gel chromatography is worse, so that any closely migrating DNA/protein complexes on gel shift assay may not be resolved at all on gel chromatography. In addition, while gel shift assays allow the side-by-side comparison of several samples, since the gel typically accommodates 10–20 lanes, only one sample per run can be injected on a gel chromatography column, eliminating side-by-side comparisons and reducing sample throughput.

Although the clinical significance of detecting DNA is well known and the clinical need to detect various proteins is well known, there is no appreciation for the clinical detection of DNA-binding proteins except autoantibodies to DNA.

SUMMARY OF THE INVENTION

The present invention relates to new and improved methods of detecting polychlorinated dibenzodioxins, polychlorinated dibenzofurans, polychlorinated biphenyls, and structural analogues thereof which exhibit biological activity characteristic of such compounds. These compounds bind to a heteromer formed from a plurality of proteins, one of which is an Ah receptor in inactive form. The binding of such ligands to the Ah receptor causes a complex containing active Ah receptor bound to the ligand to dissociate from the heteromer. The presence of this complex can be detected and used to determine the presence and amount of polychlorinated dibenzodioxins, polychlorinated dibenzofurans, polychlorinated biphenyls, and the like, in a test sample. The present invention relates to new and improved methods for assaying dioxin-like compounds by detecting transformed Ah receptor.

The methods of the present invention were discovered in attempts to reduce background and increase sensitivity of the assay for dioxin-like compounds. Assays were constructed that used the dioxin responsive element (DRE) as binding substance for the transformed Ah receptor while non-transformed Ah receptor is "washed away". However, tests have shown that incubation of the non-bound Ah receptor can start to bind DRE. After ruling out possible sources of contamination, the studies suggested that at least some of the background is related to "spontaneously", or at least Dioxin independent, transforming receptor.

Thus methods of detecting Ah receptor bound to DRE by immuno assays using antibodies to the Ah receptor were of limited sensitivity because of the background noise. Furthermore, a sandwich immuno assay techniques using the anti-Ah receptor antibodies required binding the transformed Ah receptor to nitrocellulose. One of the discoveries of the present invention is that anti-ARNT antibodies are superior to the present anti-Ah receptor antibodies as a detection label and will bind to the transformed Ah receptor complex. Using an anti-ARNT detection system allows the construction of a sandwich immunoassay so that binding transformed Ah receptor to nitrocellulose is eliminated.

The present invention includes the method of detecting dioxin-like compounds consisting essentially of the group of compounds: polychlorinated dibenzodioxins, polychlorinated dibenzofurans, polychlorinated biphenyls, and structural analogues thereof which exhibit biological activity characteristic of polychlorinated dibenzodioxins, polychlorinated dibenzofurans, polychlorinated biphenyls. The assay includes an inactive Ah receptor in a form capable of binding to the dioxin-like compounds and being transformed to an active form that forms a complex with ARNT and binds a dioxin responsive element. A test sample is contacted with the assay under conditions effective to bind the dioxin-like compounds to the Ah receptor and allow transformation of the Ah receptor to an active form that forms a complex with ARNT. The presence of the complex containing the transformed Ah receptor and the ARNT is detected with an antibody with a region capable of binding to the ARNT when associated with the complex.

The heteromer containing the Ah receptor can be obtained from any number of sources. Although the heteromer has been identified in several human tissues and cells in culture, including lung, liver, kidney, placenta, B lymphocytes, and thymus, it is preferably obtained from other mammals for ease of availability. A particularly preferred source of the heteromer is a cytosol fraction of mammalian hepatocytes. When the Ah receptor is obtained from liver cytosol, generally, all of the proteins and enzymes necessary for transformation of the Ah receptor are present. Because the transformation is natural part of the cell processes, it would be expected that these proteins and enzymes would exist in the proper ratios for complete transformation of the Ah receptor. One of the discoveries of the present invention is that the level of ARNT in the cytosol is a limiting factor to the transformation of the Ah receptor. Therefore, the addition of recombinant ARNT has greatly reduced the background noise and improved the detection limits of the Ah receptor dioxin assay.

The present invention includes the method of detecting dioxin-like compounds consisting essentially of the group of compounds: polychlorinated dibenzodioxins, polychlorinated dibenzofurans, polychlorinated biphenyls, and structural analogues thereof which exhibit biological activity characteristic of polychlorinated dibenzodioxins, polychlorinated dibenzofurans, polychlorinated biphenyls. The assay includes: 1) an inactive Ah receptor in a form capable of binding to the dioxin-like compounds and being transformed to an active form that forms a complex with ARNT and binds a dioxin responsive element, and 2) a quantity of ARNT sufficient to optimize Ah receptor transformation. A test sample is contacted with the assay under conditions effective to bind the dioxin-like compounds to the Ah receptor and allow transformation of the Ah receptor to an active form that forms a complex with ARNT. The presence of the complex containing the transformed Ah receptor and the ARNT is detected.

An effort to produce an assay for dioxin-like compounds that would cure the deficiencies of the above assays, estimate TEQs directly, and be performed totally in vitro is described herein. This assay measures the in vitro binding and transformation of the Ah receptor by detecting the ability of the receptor to bind DREs in the presence of excess ARNT using affinity chromatography with subsequent immunoassay of the transformed Ah receptor with anti-ARNT antibodies.

DETAILED DESCRIPTION

Figure 1:
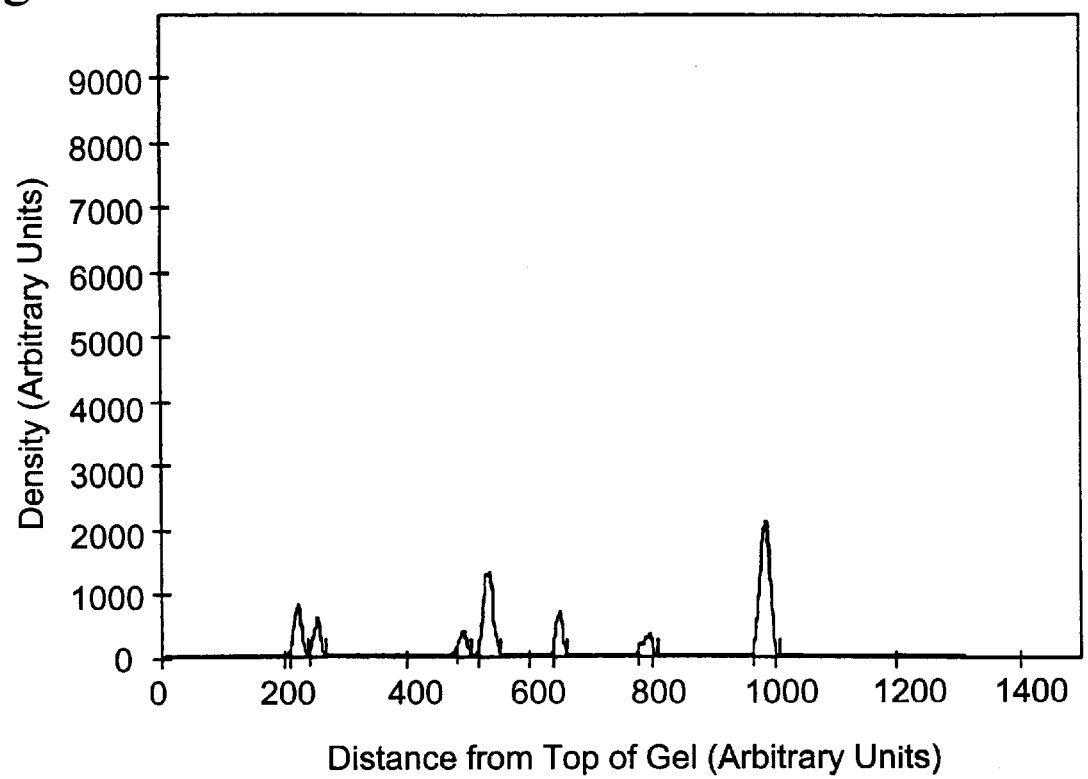
FIG. 1 is a densitometric scan of an immunoblot of an assay for transformed Ah receptor/ARNT complex after size exclusion chromotagraphy of a test sample without a dioxin-like compound.

The process by which the dioxin-like compounds bind to the Ah receptor and cause the active Ah receptor bound to the ligand to dissociate is-known as transformation. The inactive Ah receptor exists as one of at least three proteins which form a cytosolic high molecular weight heteromer. Although the precise composition and structure of the heteromer is unknown, it is believed that heat shock protein 90 is another one of the constituent proteins. Upon ligand binding to the Ah receptor, the Ah receptor dissociates from the complex and undergoes a conformational change to a heterodimer complex that has increased affinity for cationic exchangers and double stranded DNA. This process of activating the Ah receptor is essentially irreversible. In living cells, activated Ah receptor bound to a ligand enters the nucleus and may bind to the nuclear regulatory sequence of several genes. One such sequence is known as the dioxin responsive element ("DRE"), and interactions between it and the activated Ah receptor are believed to lead to enhanced gene expression. Although the Ah receptor with dioxin-like compound ligands are not themselves toxins, the enhanced gene expression caused by its binding to the dioxin responsive element is believed to be the basis of the toxic response to dioxin-like compounds. The transformation phenomena is discussed in more detail in G. P. Landers et al., "Review Article—The Ah Receptor and the Mechanism of Dioxin Toxicity,"Biochem. J., vol. 26, pp. 273–87 (1991) and S. Safe, "Polychlorinated Biphenyls (PCBs), Dibenzo-Dioxins (PCDDs), Dibenzofurans (PCDFs), and Related Compounds: Environmental and Mechanistic Considerations Which Support the Development of Toxic Equivalency Factors (TEFs)," Toxicology, vol. 21, pp. 51–87 (1990).

For the present invention, the heteromer containing the Ah receptor can be obtained from any number of sources. Although the heteromer has been identified in several human tissues and cells in culture, including lung, liver, kidney, placenta, B lymphocytes, and thymus, it is preferably obtained from other mammals for ease of availability. The heteromer is present in rodent liver, thymus, lung, kidney, brain, testis, and skeletal muscle cells. A particularly preferred source of the heteromer is a cytosol fraction of mammalian hepatocytes. For example, the heteromer can be obtained by isolating liver cytosol from male Hartley guinea pigs, according to E. C. Henry, et al., "Characterization of Multiple Forms of the Ah receptor: Comparison of Species and Tissues," Biochem, 28:6430–40 (1989), and frozen or lyophilized in five milliliter aliquots contained in glass or plastic test tubes.

When the Ah receptor is obtained from liver cytosol, generally speaking all of the proteins and enzymes necessary for transformation of the Ah recptor are present. Because the transformation is natural part of the cell processes, it would be expected that these proteins and enzymes would exist in the proper ratios for complete part transformation of the Ah recpetor. One of the discoveries of the present invention it that the level of ARNT in the cytosol is a limiting factor to the transformation of the Ah receptor. Therefore, the addition of recombinant ARNT has greatly reduced the background noise and improved the detection limits of the Ah receptor dioxin assay.

The present detection method is desirably carried out in any conventional test kit format. For example, the immunoassay can be an affinity, solid phase capture or sandwich immunoassay.

A solid phase capture immunoassay test kit includes the heteromer, ARNT, an antibody capable of binding to the complex, preferably anti-ARNT and having a label to permit detection, and a solid support. The heteromer is contacted with the test sample and the resulting mixture is contacted with the solid support so that the complex binds to the support. After removal of unbound material, the antibody is contacted with-the bound, active Ah receptor complex. As a result, the label on the antibody can then be detected.

In a particularly preferred form of the present invention the mixture of heteromer and test sample can be contacted with an affinity matrix so that the complex binds to the affinity matrix. After removal of unbound material, the complex is eluted from the affinity matrix and allowed to contact and adsorb to the solid support. The labelled antibody is then contacted with the adsorbed complex to permit detection. The affinity matrix can also be used to bind to the complex and thereby separate the complex from the remainder of the test sample-heteromer mixture in the sandwich and competitive formats. In each, the complex can be subsequently eluted from the affinity matrix and into absorptive contact with the solid support.

A sandwich immunoassay kit contains a binding substance having a first region capable of binding to a solid support and a second region capable of binding to the complex, the heteromer, an antibody with a region capable of binding to the complex containing active Ah receptor bound to the ligand and having a label to permit detection of the antibody, and a solid support. In use, the binding substance is contacted with the solid support. After the binding substance binds to the solid support and the test sample is contacted with the heteromer, the mixture of test sample and heteromer is placed in contact with the solid support. As a result, the complex binds to the second region of the binding substance. Following removal of the unbound mixture, the labelled antibody is contacted with the complex bound to the solid support. As a result, the label on the antibody can be detected.

The solid support used in any of these immunoassay test kit formats may be any water insoluble, water suspendible solid material conventionally utilized in such kits. Suitable examples are polymeric membranes, plastic or glass beads, test tubes, or microtiter plates. The binding substance in the complex, containing active Ah receptor bound to the ligand, may be bound to the solid carrier by covalent binding or adsorption. When test tubes or microtiter plates are utilized, such bonding takes place at the inner walls of these carriers.

In the sandwich immunoassay test kits, the kit can be merchandised with the binding substance already bound to the solid support. Such application to the solid support surface is achieved by contacting the binding substance with the solid support and maintaining such contact for sufficient time to permit the first region of the binding substance to bond to the solid support. Typically, such contact takes one to eighteen hours, preferably four hours. The non-adhered binding substance is then separated from the insolublized binding substance (i.e., that which is bound to the solid support) and the solid support is then washed.

In all of the immunoassay test kit formats, the test sample, the heteromer and ARNT are placed in contact with each other and allowed to incubate for sufficient time to permit transformation. Typically, such transformation takes two hours. Such contact desirably, is followed by contacting the test sample and heteromer mixture with a solid support. For the solid phase capture assay, the complex binds directly to the solid support, while the complex binds indirectly (i.e., through the binding substance) to the solid support- in the competitive assay or sandwich immunoassays. For all three immunoassay test kit formats of the present invention after allowing sufficient time for incubation, residual test sample and heteromer mixture is separated from the insolublized material bound to the solid support. The insoluble material is then washed.

After the labelled antibody for the solid phase capture or the labelled analogue for the competitive immunoassay test kit are contacted with insolubilized material bound to the solid support, such contact is maintained for sufficient incubation time so that the labelled material bonds indirectly to the solid support. Typically, one hour to eighteen hours, preferably two hours, is sufficient for such binding. The unbound material is then separated from the insolubilized material, and the insolubilized material is then washed.

A labelled analogue or antibody (as the case may be) can be used to detect the extent to which that analogue or antibody indirectly bonds to the solid support. Such detection preferably involves a quantitative measurement of the labelled material. For the solid phase capture, the labeled antibody bonds directly to the complex so that the detection procedures directly determine the amount of complex formed. The label can be a colored, fluorescent, chemiluminescent, radioactive, or enzymatic material conjugated to the antibody or analogue, or a colored, fluorescent, chemiluminescent, radioactive, or enzymatic— material conjugated to a secondary binding substance such as an antibody that binds to the binding substance that interacts with the complex. For the sandwich and solid phase capture immunoassay test kits, an antibody capable of binding to the complex containing active Ah receptor/ARNT complex bound to a dioxin-like compound ligand is used. The antibodies can be in polyclonal or monoclonal form.

Enzymatic labels are well known in the art. Examples of such labels include alkaline phosphatase, horseradish peroxidase, glucose-6-phosphate, β-galactosidase, xanthine oxidase, catalase, urease, glucose oxidase, galactose oxidase, β-glucuronidase, and β-B-glucosidase. Such labels are detected by the conversion of substrates to measurable product colorimetrically, fluorometrically, and spectrophotometrically using devices well known in the art. These instruments generate an optical density value which can be converted to a dioxin-like compound concentration by comparison to a standard curve.

Alternatively, the antibody or analogue can be directly labeled. Suitable colored labels include fluorescent, chemiluminescent and colorimetric. These labels are detected by spectrophotometry or densitometry. These instruments generate an optical density value which can be converted to a dioxin-like compound concentration by comparison to a standard curve.

Suitable fluorescent labels for the antibody or analogue include fluorescein, rhodamine and their derivatives. These labels are detected by fluorimetry. These instruments generate an optical density value which can be converted to a dioxin-like compound concentration by comparison to a standard curve. Suitable chemiluminescent labels include luminol, isoluminol, acridinium esters, thioesters, sulfonamides, and phenathridinium esters. These labels generate an optical density value which can be converted to a dioxin-like compound concentration by comparison to a standard curve. Such labelling systems produce a long-lived glow of light. This glow can be detected with luminometers, photomultiplier tubes, and solid state detectors.

The sandwich immunoassays utilize a binding substance with a first region capable of binding to the solid support and a second region capable of binding to a complex containing active Ah receptor/ARNT complex bound to a dioxin-like compound ligand. The binding substance is preferably selected from the group consisting of an antibody, a dioxin responsive element, and a portion of the dioxin responsive element.

Where the binding substance is in the form of an antibody, such antibodies can be polyclonal or monoclonal. The binding substance can be composed of calf thymus DNA adsorbed or covalently coupled to a solid support or specific DNA sequences adsorbed or covalently coupled to a solid support.

It is particularly preferred to utilize the dioxin responsive element or portions thereof to form the binding substance. The DNA sequences for the dioxin responsive element of cells in various species has been the subject of extensive investigation. Dioxin responsive element nucleotide sequences are known in the art and are disclosed in D. W. Nebert, et. al., "Minireview—Regulation of the Mammalian Cytochrome P1-450(CYPIAI) Gene", Int. J. Biochem, vol. 21, no. 3, pp. 243–52 (1989), which is hereby incorporated by reference.

The immunoassays of the present invention have a number of potential uses. One use for this assay would be the one step determination of toxic equivalent factors ("TEFs"). TEFs are a measure of the toxic potential of Ah receptor-dependant toxins and can be used in the hazard and risk assessment of such compounds. The assay could be used to screen for anti-estrogenic drugs used for mammary tumor therapy. The assay could also be used to screen potential natural or synthetic TCDD antagonists which may have potential as anti-promotional agents or in cancer prevention. It could be a rapid screen for dioxin-like toxicity in pharmaceutical and agrichemical products. In basic research, the assay could be used as an endpoint in experiments for studying the cellular events that effect Ah receptor transformation in human cell lines, in order to understand human susceptibility to dioxin- like compounds. The assay could be used to determine exposure status to TCDD and dioxin-like compounds in human or animal tissues and cells, the response of human Ah receptor to TCDD and PCBs, and the levels of Ah receptor in malignant cells.

The methods of the present invention are useful for improving the detection of dioxin-like compounds in a variety of test samples. These test samples can be an environmental matrix of air, water, or soil. In addition, the assay can be used to detect dioxin-like compounds in the body fluids (e.g., blood) of humans or animals. Specifically, the present invention teaches adding ARNT in excess in the dioxin assay mixture to reduce background noise and improve detection sensitivity. ARNT can be obtained from a variety of sources and some sequences have been published. In the examples discussed herein recombinant ARNT was added in addition to the ARNT present in the guinea pig cytosol used a source of Ah receptor. ARNT was first discovered from human sources in the laboratory of Oliver Hankinson (Hoffman, E. C., Reyes, H., Chu, F. F., Sander, F., Conley, L. H., Brooks, B. A. and Hankinson, O. Cloning of a factor required for activity of the Ah (dioxin) receptor. Science 252:954–958, 1991, also Genbank accession number M69238). Rat ARNT has also been cloned and sequenced (Carver, L. A., Hogenesch, J. B. and Bradfield, C. A. Expression of Ah receptor and ARNT mRNAs in Rat Tissues. Unpublished, Genbank accession number U08986). A partial clone of mouse ARNT (Pollenz, R. S., Sattler, C. A. and Poland, A. The aryl hydrocarbon receptor and aryl hydrocarbon receptor nuclear translocator protein show distinct subcellular localizations in Hepa 1c1c7 cells by immunofluorescence microscopy. Mol.Pharmacol. 45:428–438, 1994.) exists but the full sequence, if any, has not been filed in Genbank.

Method for Preparing Guinea Pig Cytosol

The method and materials for preparing the Guinea Pig Cytosol are desbribed below. Guinea Pig Cytosol is the source of the inactive Ah receptor and ARNT, but adding additional ARNT provides a more sensitive assay.

HEDG buffer was composed of 25 mM HEPES (N-2[2-Hydroxyethyl]piperazine-N'-[2-ethansulfonic acid] Sodium salt), 1.5 mM EDTA (Ethylenediamine-tetraacetic acid Tetrasodium salt), 1 mM DTT (DL-Dithiothreitol), 10% glycerol, pH 7.6. Perfusion buffer was HEDG plus 1.15% (w/v) KCl (potassium chloride). Buffers were chilled on ice before use.

Male Hartley guinea pigs weighing 300–350 g were obtained from Cornell Research Animal Resources, Cornell University, Ithaca, N.Y. Guinea pigs were anaesthetized and killed with carbon dioxide. Livers were perfused in situ with 100 mL ice-cold perfusion buffer, excised, trimmed of connective tissue, poorly perfused liver and gall bladder and weighed. The liver was minced and five mL of ice-cold HEDG per gram liver were added and the whole homogenized in a 50 mL homogenizer with teflon pestle using at 200 rpm for a total of seven strokes. Crude homogenate was centrifuged at 12,500 RPM in 50 mL tubes in a JA17 rotor in a Beckman J2-MI preparative centifuge at 4 degrees C for 20 minutes.

Post-centifugation lipid was removed by aspiration and discarded. The supernatant was poured off the pellet and saved. Pooled supernatants were centifuged for 60 min at 4 degress C at 37,000 RPM in 25 mL ultracentrifuge tubes in a 70 TI rotor in a Beckman ultracentrifuge model L8-70M.

Lipid was removed by aspiration and the supernatants poured off the pellets, and the supernatants pooled. Supernatants were aliquoted and frozen at −80 degrees C until used.

Procedure for Synthesis of Transformed Ah Receptor Affinity Gel for mini-Ah Immuno Assay from DRE oligonucleotides and cyanogen-bromide-activated sepharose 4B.

One of the preferred embodiments for practicing the methods of the present invention is an affinity matrix. The procedure for attaching the DRE binding elements to cyanogen-bromide-activated sepharose 4B is disclosed below. (Coupling to cyanogen-bromide-activated sepharose 4B: Kanonaga J. T. and R. Tjian (1986) Affinity purification of sequence-specific DNA binding proteins. PNAS 83: 5889–5893.)

Buffer preparation: High purity 18 megaohm per cm deionized water was used for all preparations. 6N NaOH was prepared by dissolving 120 g sodium hydroxide in 400 mL water and adjusting the volume to 500 mL. MOPS/EDTA buffer (25 mM MOPS, 0.2 mM EDTA, pH 7.6) was prepared by dissolving 1.31.g MOPS (3-[N-morpholino] propane-sulfonic acid), 0.019 g EDTA ((Ethylenediamine-tetraacetic acid Tetrasodium salt) in 200 mL water. pH was adjusted to 7.6 with 6 N sodium hydroxide and the voulume adjusted to 250 mL. 6N potassium hydroxide was prepared by dissolving 168 g potassium hydroxide in 400 mL water and adjusting the volume to 500 mL. 1 mM HCl was prepared by pipetting 165 uL concentrated HCl (12. 1N) into 2000 mL water. 10 mM Potassium Phosphate buffer was prepared by dissolving 1.15 g concentrated phosphoric acid (85%, HPLC grade) in 900 mL water and adjusting the pH to 8.0 using 6N potassium hydroxide, then adjusting the volumne to 1000 mL. 1M ethanolamine pH 8.0 was prepared by weighing out 61 g ethanolamine and dissolving in 800 mL water. pH was adjusted to 8.0 with concentrated HCl. 1M potassium phosphate buffer was prepared by weighing out 115 g phosphoric acid (85%, HPLC grade) and dissolving in 600 mL water. The pH was adjusted to 8.0 with 6N potassium hydroxide and the volume adjusted to 1000 mL. 1 M potassium chloride was prepared by dissoving 74.56 g potassium chloride in 800 mL water, adjusting volume to 1000 mL, and filtering through coarse filter paper. 2% sodium azide was prepared by dissolving 2 g sodium azide in 80 mL water and adjusting the volume to 100 mL. Storage buffer (10 mM Tris-HCl, 300 mM NaCl, 1 mM EDTA, 0.02% sodium azide,, pH 7.6) was prepared by dissolving 1.58 g tris-HCl, 17.5 g sodium chloride, 0.380 g EDTA (Ethylenediamine-tetraacetic acid Tetrasodium salt) in 900 mL water. pH was adjusted to 7.6 with 6N sodium hydroxide. Ten mL of 2% sodium azide was added and the whole adjusted to 1000 mL. All buffers except 6N Sodium hydroxide and 6N potassium hydroxide were chilled to 4 degrees C prior to use.

DNA sythesis and hybridization: DRE oligonucleotides were synthesized under contract by Midland DNA or Genosys and had the following sequences:

SEQ ID 1 - DRE-D: 5'-GAT CCG GAG TTG CGT GAG AAG AGC CA-3'

SEQ ID 2 - ERD-D: 5'-TGG CTC TTC TCA CGC AAC TCC GGA TC-3'

SEQ ID 3 - B-ERD: BIOTIN-5'-TGG CTC TTC TCA CGC AAC TCC GGA TC-3'

SEQ ID 4 - F-ERD: FLUORESCEIN-5'-TGG CTC TTC TCA CGC AAC TCC GGA TC-3'

Oligonucleotides were dissolved in MOPS/EDTA buffer to a concentration of 0.5 nmol per mL and stored at −80 degrees C until used. For hybridization, 420 uL each of DRE-D and ERD-D were mixed in a 1.5 mL microfuge tube and placed in for 5 min in 350 mL water contained in a liter beaker maintained at 90 degrees C. After 5 min the entire beaker was placed in a larger water bath for 4 hours maintained at 37 degrees C.

DRE hybridization and TARAC synthesis: Cyanogen-bromide-activated-sepharose 4B gel (Pharmacia, Piscataway, N.J.) was warmed to room temperature and 6.84 g dried gel weighed out. The weighed dried gel was placed in a scintered glass funnel attached to an side-arm flask and vacuum aspirator and the beads were washed sequentially with ice-cold 1 mM HCl (1500 mL), water (1800 mL), 10 mM potassium phosphate buffer (240 mL) and allowed to drain to a moist cake. the cake was transferred to a 50 mL conical polypropylene tube. An additional 9.6 mL of 10 mM potassium phosphate buffer was added and the gel stirred with a teflon stick to remove air bubbles. The hybridized DRE was added and the gel/DRE mixture was incubated at room temperature for 16.5 hours with gentle rocking. After 16.5 hours the slurry was adjusted to 50 mL with 10 mM potassium phosphate buffer, placed in a scintered glass funnel attached to a side-arm flask/vacuum aspirator. The excess buffer was removed by aspiration and saved for coupling effeciency determination as described below. The resulting gel was then washed sequentially with ice-cold water (1200 mL), 1 M ethanolamine (600 mL) and allowed to dry to a moist cake. The cake was again transferred to a conical tube and 30 mL 1 M ethanolamine was added, the whole stirred gently with a teflon stick to remove air bubbles, and incubated at room temperature for 6 hours with gentle rocking. After 6 hours incubation, the gel was washed on the scintered glass funnel sequentially with ice cold 10 mM potassium phosphate bufer (300 mL), 1 M potassium phosphate buffer (600 mL), 1 M potassium chloride (600 mL), and storage buffer (600 mL). The gel was allowed to dry to a moist cake and transferred to a conical tube. The volume was of the slurry was adjusted to 50 mL with storage buffer and the gel slurry stored at 4 degrees C until use.

ARNT, anti-ARNT & anti-Ah receptor

ARNT: Purified recombinant ARNT (Ah Receptor Nuclear Translocator) was a gift of Dr. Chris Bradfield. Preparation of ARNT is described in Chan, W. K., Chu, R., Jain, S., Reddy, J. K. and Bradfield, C. A. Baculovirus expression of the Ah receptor and Ah receptor nuclear translocater. Evidence for additional dioxin responsive element-binding species and factors required for signaling. J.Biol.Chem. 269:26464–26471, 1994. Stock recombinant ARNT was 1 mg/mL.

anti-ARNT: anti-ARNT #30-3B is a polyclonal affinity purified antibody to recombinant aa318-773 of mouse ARNT. It was a gift of Dr. Alan Poland and is decribed in Pollenz, R. S., Sattler, C. A. and Poland, A. The aryl hydrocarbon receptor and aryl hydrocarbon receptor nuclear translocator protein show distinct subcellular localizations in Hepa 1c1c7 cells by immunofluorescence microscopy. Mol.Pharmacol. 45:428–438, 1994. Concentration of anti-ARNT stock was 110 ug/mL Buffers and reagents for anti-Ah receptor antibody conjugation to alkaline phosphatase: 0.5 M Dibasic phosphate stock, Sodium Phosphate dibasic anhydrous, 71 g, dissolved in 1L water. 0.5 M Monobasic phosphate stock, Sodium Phosphate monobasic monohydrate, 69 g dissolved in in 1L water. 0.1 M phosphate buffer, pH 6.8 was prepared by mixing 92.6 mL of 0.5 M Dibasic phosphate stock and 107.4 mL of 0.5 M Monobasic phosphate stock and diluting to 1000 mL with water. 10X PBS was prepared by dissolving 81.8 g sodium chloride, 2.01 g potassium chloride, 14.2 g Sodium Phosphate dibasic anhydrous, 2.45 g potassium phosphate monobasic in 900 mL water and adjusting pH to 1000 mL. PBS was prepared by diluting 100 mL 10X PBS to 1000 mL with water. 1 M ethanolamine pH 7.0 was prepared by dissolving 61 g ethanolamine in 800 mL water and adjusting the pH to 7.0 with concentrated HCl, then adjusting volume to 1000 mL.

Antigen for anti-Ah: The amino-terminal sequence of mouse Ah receptor described by Poland et al. (Poland A, Glover E, Bradfield C. Characterization of polyclonal antibodies to the Ah receptor prepared by immunization with a synthetic peptide hapten. Molec. Pharmacol. 1991; 39: 20–26.) was synthesized with cysteine on the ultimate and norleucine as the penultimate amino-terminal residues. The full sequence used was:

SEQ ID 5 - Ah receptor antigen: Cys-Nle-Arg-Lys-Arg-Arg-Lys-Pro-Val-Gly-Lys-Thr-Val-Lys-Pro-Ile-Pro-Ala-Glu-Gly-Ile-Lys.

The peptide (Ah receptor antigen) was coupled through the cysteine to ovalbumin via an m-maleimidobenzoyl-N-hydroxysuccinimide ester bridge (Pierce, Rockford, Ill.) according to the manufacturer's directions. Antisera were produced in rabbits as described by Poland et al. Anti-Ah receptor antibodies were purified from the sera on an affinity column made from the peptide linked to iodoacetamide derivatized agarose beads according to manufacturer's directions (Pierce, Rockford, Ill.). The purified antibody was coupled to alkaline phosphatase as follows. Ten mg of antibody in a volume of 0.5 mL was mixed with 5 mg calf intestine alkaline phosphatase in a volume of 0.5 mL (Pierce, Rockford, Ill.) and dialyzed overnight against three changes of 1 liter each 0.1 M sodium phosphate buffer overnight. The dialyzed mixture was collected and 50 uL of 1% glutaraldehyde (Sigma, St. Louis Mo.) added and the whole stirred slowly for 5 min. Additional incubation at room temperature for 3 hours was followed by addition of 100 uL 1 M ethanolamine pH 7.0, 2 hour incubation at room temperature, and dialysis overnight against three changes of 1 L each PBS. The dialyzed conjugate was collected and centifuged at 13,000 g for 20 min and the supernatant collected. Two volumes Superfreeze (Pierce, Rockford, Ill.) and 1/100 volume 2% sodium azide were added and the conjugate and stored at 4 degrees C until use.

Procedure for the mini-Ah Immuno Assay

Preparation of Buffers: 155 uM TCDD stock was prepared by dissolving 1 mg 2,3,7,8-tetrachloro-dibenzo-p-dioxin (Cambridge Isotope Labs) in 20 mL DMSO (dimethylsulfoxide) overnight. 10 uM working dilution of TCDD was prepared by diluting 0.129 mL of the stock with 1.871 mL DMSO. 4M NaCl/HEDG was prepared by adding 116.88 g sodium chloride to 300 mL HEDG and adjusting the volume to 500 mL with HEDG. 0.3 M NaCl/HEDG was prepared by diluting 1.5 mL 4 M NaCl/HEDG to 20 mL with HEDG 0.6 M NaCl/HEDG was prepared by diluting 3.0 mL 4 M NaCl/HEDG to 20 mL with HEDG TBST was prepared by dissolving 1.18 g Tris-base, 6.35 g Tris-HCl, 8.76 g NaCL, and 2 mL Tween 20 in 800 mL water, adjusting volume to 1000 mL. Blocker was prepared by dissolving 10 g non-fat dry milk (Carnation) in 200 mL TBST. AP development buffer was prepared by dissolving 11 g Tris-base, 1.6 g Tris-HCl, 5.84 g Sodium Chloride, 10.2 g Magnesium Chloride hexahydrate, in 800 mL water and adjusting the volume to 1000 mL. BCIP stock was prepared by dissolving 100 mg BCIP (5-Bromo-4-Chloro-3-Indolyl Phosphate) in 2 mL N,N-Dimethylformamide, aliquoting into 66 uL portions, and freezing at −20 C until use. NBT stock was prepared by dissolving 250 mg NBT (Nitro Blue Tetrazolium) in 25 mL water, aliquoting into 660 uL proportions, and storing at −20 C until use. BCIP/NBT developer was prepared immediately before use by mixing one 66 uL aliquot of BCIP and one 660 uL aliquot of NBT in 20 mL AP development buffer.

Preparation of materials: For each mini-Ah Immunoassay sample, an empty column barrel was prepared by punching a disk from a Whatman GF/B microfibre filter using a #2 brass cork borer and inserting the punched-out disk in the bottom of a 1 mL tuberculin syringe barrel. Any number of column barrels can be prepared ahead of time. For each mini-Ah Immunoassay experiment, a 3 inch by 4.5 inch nitrocellulose membrane (BioRad, Hercules Calif.) was soaked in HEDG.

For a typical mini-Ah immunoassay utilizing 12 samples, 5 mL of Transformed Ah Receptor Affinity Gel slurry described above was pipeted into a 50 mL conical tube. The slurry was washed with 40 mL HEDG and centifuged at 1000 g for 5 min, the supernatant withdrawn and discarded, the pellet washed with 40 mL HEDG, and centrifuged again. After the second centrifugation all but 5 mL of supernatant was withdrawn and the gel thus resuspended in the original volume. 10 mL guinea pig hepatic cytosol was thawed. The thawed cytosol was pooled and then divided into two 5 mL groups and treated with either 5 uL DMSO or 5 uL 10 uM TCDD in DMSO.

Assembly of transformation mixture:In the preferred embodiment of the mini-Ah immunoassay, each sample was composed of one 1.5 mL microfuge tube with the following sequential additions: 90 uL 4 M NaCl/HEDG, 400 uL Transformed Ah Receptor Affinity Gel slurry and 800 uL cytosol (treated with DMSO or TCDD as described above). The three components described above are the minimum components added at that step of the mini-Ah immunoassay. Any additional materials, such as ARNT, anti-ARNT and anti-Rabbit/alkaline phosphatase conjugate, were sometimes also added at this time as described in the specific examples. After assembly of the samples, the tubes were capped and the samples incubated at room temperature for 2 hours with gentle rocking to allow transformation of the Ah receptor to take place, interaction of transformed Ah receptor and ARNT, and binding of the transformed Ah receptor as a heteromer to the DRE oligonucleotide contained on the Transformed Ah Receptor Affinity Gel.

Isolation transformed Ah receptor: After the 2 hour incubation the mixtures were pipetted into the empty column barrels and allowed to drain. The Transformed Ah Receptor Affinity Gel, retained by the microfibre disk, was then washed sequentially with 1 mL HEDG, and twice with 400 uL 0.3 M NaCl/HEDG.

The HEDG-soaked nitrocellulose membrane was then inserted into an ELIFA apparatus (Pierce, Rockford, Ill.) according to the manufacturer's instructions and 10 mL syringes were fitted to each of the two luer lock valves supplies on the apparatus. The washed columns were then inserted into any of the 96-well recepticals of the ELIFA apparatus. Bound transformed Ah receptor complex was eluted by addition of 2 washes of 400 uL each 0.6 M NaCl/HEDG. Simultaneous vacuum was applied by drawing out the two 10 mL syringes fitted to the ELIFA, therby drawing the eluted materials from the column thru the nitrocellulose sheet and binding any proteins to the sheet.

Immunoprobing of transformed Ah receptor: The nitrocellulose membrane was then removed from the ELIFA apparatus, rinsed briefly with water, and placed in 20 mL blocker containing test antibody. All antibodies were incubated with the nitrocellulose membrane for one hour at room temperature. When the test antibody was anti-Ah receptor/ alkaine phosphatase conjugate, 100 uL anti-Ah receptor/ alkaline phosphatase conjugate (1:200), per 20 mL blocker was used. When anti-ARNT was added to the transformation mixture, anti-Rabbit/alkaline phosphatase conjugate (Sigma, St. Louis, Mo.) diluted 1:1000 (20 uL to 20 mL blocker) was used to probe the membrane. When ARNT, anti-ARNT and anti-Rabbit or anti-ARNT and anti-Rabbit was added to the transformation mixture, the Immunoprobing step was eliminated.

Immunodetection and densitometry: In all cases the nitrocellulose membrane was rinsed prior to immunodetection 3 times for 5 min each with 100 mL TBST, briefly washed in AP development buffer and developed in freshly made BCIP/NBT developer for 5 min, whereupon the color reaction was stopped by washing the membrane in water.

Quantitative data were obtained by scanning the dried membrane in a Microtek 600ZS scanner in gray scale, 300 dpi, 0% brightness, 0% contrast. Densitometric measurements of the dot-blots were made using ScanAnalysis software (Biosoft, Cambridge U.K.).

EXAMPLE 1

Effect of addition of ARNT to TCDD-dependent transformation of Ah receptor Method Cytosol & DRE affinity gel are prepared as described above. Cytosol is dosed with 1:1000 v/v DMSO (−) or 1:1000 v/v 10 uM 2,3,7,8-tetrachlorodibenzo-p-dioxin in DMSO (+).

Samples

| protocol | code | cytosol | DRE gel | ARNT |
|---|---|---|---|---|
| normal | E | (−) 800 uL | 400 uL | |
| | F | (−) 800 uL | 400 uL | |
| | G | (+) 800 uL | 400 uL | |
| | H | (+) 800 uL | 400 uL | |
| arnt spike | I | (−) 800 uL | 400 uL | 2 ug |
| | J | (−) 800 uL | 400 uL | 2 ug |
| | K | (+) 800 uL | 400 uL | 2 ug |
| | L | (+) 800 uL | 400 uL | 2 ug |

Results

| protocol | code | spot density | average1 | difference2 |
|---|---|---|---|---|
| normal | E | 112848 | | |
| | F | 87986 | 100417 | |
| | G | 157620 | | |
| | H | 142115 | 149868 | 49541 |
| arnt spike | I | 81100 | | |
| | J | 77264 | 79182 | |
| | K | 308831 | | |
| | L | 298526 | 303679 | 224497 |

1. data represent the average of two replicates
2. data represent the difference between TCDD treated (+) and DMSO treated (−) samples for that protocol.

Conclusions

ARNT addition at 2 ug/assay increased TCDD-dependent response 354%. ARNT addition did not increase non-TCDD dependent transformation of the Ah receptor. Therefore, ARNT must be a limiting factor in cytosol. Addition of ARNT in excess will enhance binding of TCDD-transformed Ah receptor to the DRE and improve signal-to-noise considerably.

EXAMPLE 2

Effect of addition of ARNT at 2 concentrations on TCDD-dependent transformation of Ah receptor Method Cytosol and DRE affinity gel are prepared as described above. Cytosol is dosed with 1:1000 v/v DMSO (−) or 1:1000 v/v 10 uM 2,3,7,8-tetrachlorodibenzo-p-dioxin in DMSO (+).

Samples

| protocol | code | cytosol | DRE gel | ARNT |
|---|---|---|---|---|
| 0.5 ug arnt | 1 | (−) 800 uL | 400 uL | 0.5 ug |
| | 2 | (−) 800 uL | 400 uL | 0.5 ug |
| | 3 | (+) 800 uL | 400 uL | 0.5 ug |
| | 4 | (+) 800 uL | 400 uL | 0.5 ug |
| 2.0 ug arnt | 5 | (−) 800 uL | 400 uL | 2 ug |
| | 6 | (−) 800 uL | 400 uL | 2 ug |
| | 7 | (+) 800 uL | 400 uL | 2 ug |
| | 8 | (+) 800 uL | 400 uL | 2 ug |

Results

| protocol | code | spot density | average1 | difference2 |
|---|---|---|---|---|
| 0.5 ug arnt | 1 | 40788 | | |
| | 2 | 47934 | 44361 | |
| | 3 | 184049 | | |
| | 4 | 164371 | 174210 | 129849 |
| 2.0 ug arnt | 9 | 62498 | | |
| | 10 | 58223 | 60361 | |
| | 11 | 281912 | | |
| | 12 | 258302 | 270107 | 209747 |

1. data represent the average of two replicates
2. data represent the difference between TCDD treated (+) and DMSO treated (−) samples for that protocol.

Conclusions 0.5 ug arnt gave less response than 2 ug ARNT so it is likely that the effect of ARNT will probably show a dose response with more dosages. The optimimum amount of ARNT that produces maximum response is determined by adding increasing amounts of ARNT to generate a dose response curve. The dosage of ARNT at the top of the curve would be used and would vary depending upon the cytosol used for the orginal source of tha Ah receptor and ARNT.

EXAMPLE 3 anti-ARNT Recognizes the Transformed Ah Receptor Complex Bound to DRE

Cytosol and DRE affinity gel are prepared as described above. Cytosol is dosed with 1:1000 v/v DMSO (−) or 1:1000 v/v 10 uM 2,3,7,8-tetrachlorodibenzo-p-dioxin in DMSO (+).

Assembly of transformation mixture is as described above, with the addition of anti-ARNT as shown in the table below.

Assembly of transformation mixture

| protocol | code | cytosol | DRE | anti-ARNT |
|---|---|---|---|---|
| Normal | A | (−) 800 uL | 400 uL | — |
|  | B | (−) 800 uL | 400 uL | — |
|  | C | (+) 800 uL | 400 uL | — |
|  | D | (+) 800 uL | 400 uL | — |
| 200 ng anti-ARNT spike | E | (−) 800 uL | 400 uL | 2 uL |
|  | F | (−) 800 uL | 400 uL | 2 uL |
|  | G | (+) 800 uL | 400 uL | 2 uL |
|  | H | (+) 800 uL | 400 uL | 2 uL |
| 660 ng anti-ARNT spike | I | (−) 800 uL | 400 uL | 6 uL |
|  | J | (−) 800 uL | 400 uL | 6 uL |
|  | K | (+) 800 uL | 400 uL | 6 uL |
|  | L | (+) 800 uL | 400 uL | 6 uL |

Immunoprobing of transformed Ah receptor is as described above with the following probes. Transformed Ah receptor was detected with anti-Ah Receptor/alkaline phosphatase conjugate as described above for samples A,B,C,D. For samples E-L, the assay for transformed Ah receptor was performed as described above except anti-rabbit/alkaline phosphatase conjugate (Sigma, cat # A3687) at 1: 1000 dilution was used as the probe in order to detect anti-ARNT bound to the transformed Ah receptor complex. Immunodetection and densitometry is as described above.

Results

| protocol | code | density | average1 | difference2 |
|---|---|---|---|---|
| Normal | A | 94630 |  |  |
|  | B | 89899 | 92265 |  |
|  | C | 177175 |  |  |
|  | D | 162801 | 169988 | 77724 |
| 220 ng anti-ARNT spike | E | 19597 |  |  |
|  | F | lost | 19597 |  |
|  | G | 191233 |  |  |
|  | H | 219762 | 205498 | 185901 |
| 660 ng anti-ARNT spike | I | 75330 |  |  |
|  | J | 67559 | 71445 |  |
|  | K | 231412 |  |  |
|  | L | 291157 | 261285 | 189840 |

1. data represent the average of two replicates
2. data represent the difference between TCDD treated (+) and DMSO treated (−) samples for that protocol.

Conclusions

Anti-ARNT mixed with DREs and cytosol recognized complexed/DRE bound ARNT. Anti-ARNT can bind ARNT and still allow it to form a complex with DRE and Ah receptor. Anti-ARNT recognizes TCDD-dependent transformed Ah receptor complex. No difference was seen comparing 2 uL anti-ARNT and 6 uL anti-ARNT. This experiment shows that anti-ARNT can be used in a sandwich-type format to detect TCDD-dependent transformation of Ah receptor to the DRE-binding form. anti-ARNT is superior to anti-Ah receptor as a detection ligand for the TCDD-dependent transformation of Ah receptor to the DRE-binding form.

EXAMPLE 4

Effect of adding ARNT, anti-ARNT and anti-rabbit/alkaline phophatase to transformation reaction.

Method

Cytosol and DRE affinity gel are prepared as described above. Cytosol is dosed with 1:1000 v/v DMSO (−) or 1:1000 v/v 10 uM 2,3,7,8-tetrachlorodibenzo-p-dioxin in DMSO (+).

Samples

| protocol | code | cytosol | DRE | ARNT | aARNT1 | aRb2 |
|---|---|---|---|---|---|---|
| arnt/anti-ARNT | 1 | (−) 800 uL | 400 uL | 2 ug | 2 uL | — |
|  | 2 | (−) 800 uL | 400 uL | 2 ug | 2 uL | — |
|  | 3 | (+) 800 uL | 400 uL | 2 ug | 2 uL | — |
|  | 4 | (+) 800 uL | 400 uL | 2 ug | 2 uL | — |
| arnt/anti-ARNT/anti-rabbit | 5 | (−) 800 uL | 400 uL | 2 ug | 2 uL | 2 uL |
|  | 6 | (−) 800 uL | 400 uL | 2 ug | 2 uL | 2 uL |
|  | 7 | (+) 800 uL | 400 uL | 2 ug | 2 uL | 2 uL |
|  | 8 | (+) 800 uL | 400 uL | 2 ug | 2 uL | 2 uL |
| anti-ARNT/anti-rabbit | 9 | (−) 800 uL | 400 uL | — | 2 uL | 2 uL |
|  | 10 | (−) 800 uL | 400 uL | — | 2 uL | 2 uL |
|  | 11 | (+) 800 uL | 400 uL | — | 2 uL | 2 uL |
|  | 12 | (+) 800 uL | 400 uL | — | 2 uL | 2 uL |

1. anti-ARNT
2. anti-rabbit/alkaline phosphatase conjugate

Immunoprobing of transformed Ah receptor is as described above with the following probes. Samples 1–4 were probed with anti-rabbit/alkaline phosphatase conjugate (Sigma, cat # A3687) at 1:1000. Samples 5–12 were developed directly without probing. Immunodetection and densitometry is as described above.

Results

| protocol | code | density | average1 | difference2 |
|---|---|---|---|---|
| Normal | 1 | 13813 |  |  |
|  | 2 | 3380 | 8597 |  |
|  | 3 | 233321 |  |  |
|  | 4 | 254942 | 244132 | 235535 |
| ARNT/anti-ARNT/anti-rabbit | 5 | 2879 |  |  |
|  | 6 | 10364 | 6622 |  |
|  | 7 | 85215 |  |  |
|  | 8 | 80175 | 82695 | 76074 |
| anti-ARNT/anti-rabbit | 9 | 2809 |  |  |
|  | 20 | 2808 | 2809 |  |
|  | 11 | 36309 |  |  |
|  | 12 | lost | 36309 | 33501 |

Conclusion

It is possible to add anti-rabbit and anti-ARNT together with cytosol/DRE and eliminate all antibody incubation steps. This suggests that an assay without capturing the transformed Ah receptor complex can be detected by labeling the ARNT, however, the addition of anti-rabbit in separate step works better. This means that the closer the label comes to the complex (i.e. ARNT or labeled anti-ARNT) the better the assay is predicted to work. The addition of ARNT improves response, consistent with previous experiments.

EXAMPLE 5

Test Size Exclusion Column format with labeled DRE, labeled ARNT, and co-labeled DRE and ARNT Size-exclusion column: 10 mL bed volume sephacryl S-100-HR (Sigma, St. Louis, Mo.) packed in Econopac column (Biorad cat. no. 732-1010), equilibrated in HEDG plus 200 mM NaCl. Column was hooked up to a peristaltic pump. Flow rate was 0.5 mL/min. The size exclusion column outlet was attached to a HPLC fluorimeter set at excitation 494 nm and emmission 520 nm to detect fluorescein. DRE used was F-ERD oligo (SEQ. ID. #4) and DRE-D oligo (SEQ. ID. #1) hybridized as described above. Cytosol was prepared as described above. Cytosol was dosed with 1:1000 v/v DMSO (−) or 1:1000 v/v 10 uM 2,3,7,8-tetrachlorodibenzo-p-dioxin in DMSO (+).

Assay tubes were set up as follows:

| Sample | Cytosol | DRE | anti-ARNT |
|--------|---------|--------|-----------|
| A | (−) 800 uL | 2 nmol | — |
| B | (+) 800 uL | 2 nmol | — |
| C | (−) 800 uL | 2 nmol | 2 uL |
| D | (+) 800 uL | 2 nmol | 2 uL |

Samples were incubated for 2 hours at room temperature as described above to achieve transformation/binding events then put on ice. The entire A sample was loaded onto the Size Exclusion Column and chromatography developed at a flow rate of 0.5 ml/min. Eluant fractions were collected at 2 min intervals (1 mL/fraction). The protocol was repeated for samples B,C,D.

The fluorimeter readings went offscale and usable readings for the fluorescent DRE were not possible. 200 uL subaliquots of fractions 3–10 were submitted to Sodium Dodecyl Sulfate—PolyAcrylamide Gel Electrophoresis (SDS-PAGE) followed by western blotting. Blots of fractions from samples A and B were probed with anti-ARNT (1:200) and anti-rabbit/alkaline phosphatase (1: 1000) and developed with BCIP/NBT. Blots of fractions from samples C and D were probed with anti-rabbit/alkaline phosphatase (1:1000) and developed with BCIP/NBT.

Results

Figure 2:
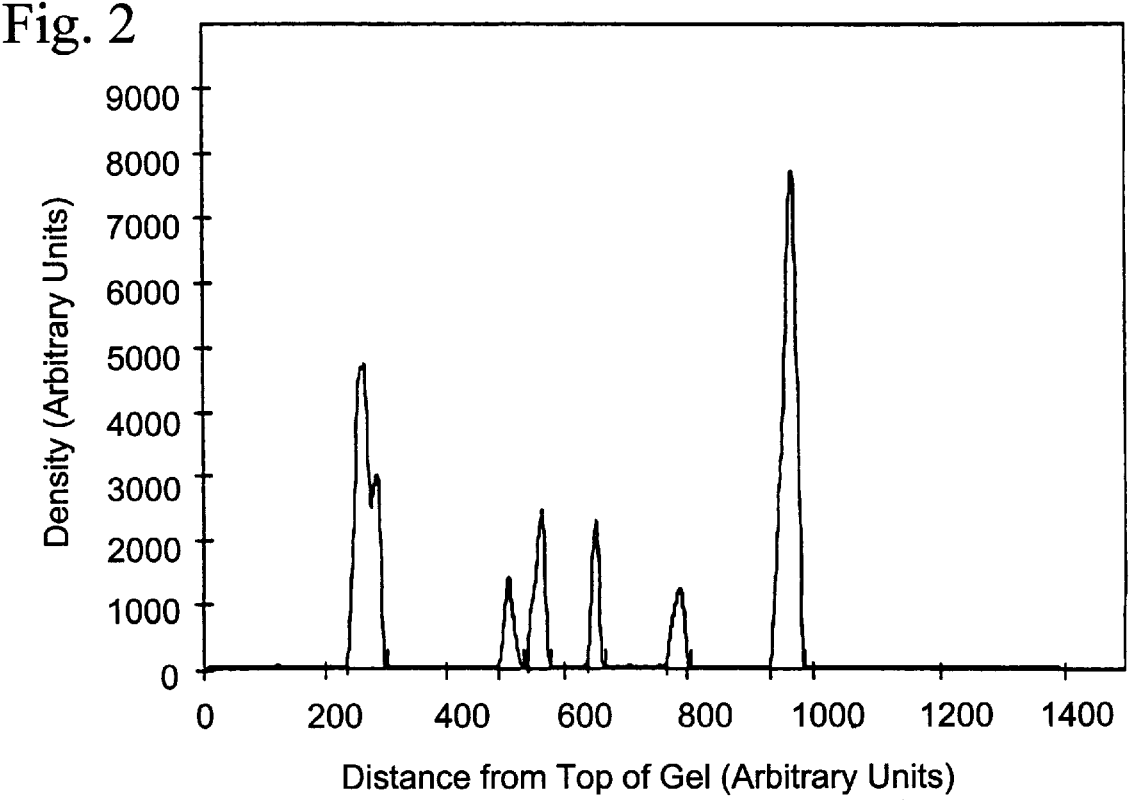
FIG. 2 is a densitometric scan of an immunoblot of an assay for transformed Ah receptor/ARNT complex after size exclusion chromotagraphy of a test sample with a dioxin-like compound.

FIG. 1 is a densitometric scam of an immunoblot of fraction 3 sample A. FIG. 2 is a densitometric scan of an immunoblot of fraction 3 sample B. Fraction 3 of sample B showed a band at the size of ARNT (circa 97 kD) that was absent in fraction 3 of sample A (The first peak from the left). These results shows that this protein migrates as a high molecular species in a TCDD dependent manner consistent with it being the ARNT part of the transformed DRE/AhR/ARNT complex. Thus size exclusion chromatography can resolve the TCDD-dependent DRE/AhR/ARNT complex from interfering substances which allows the complex to be detected.

Figure 3:
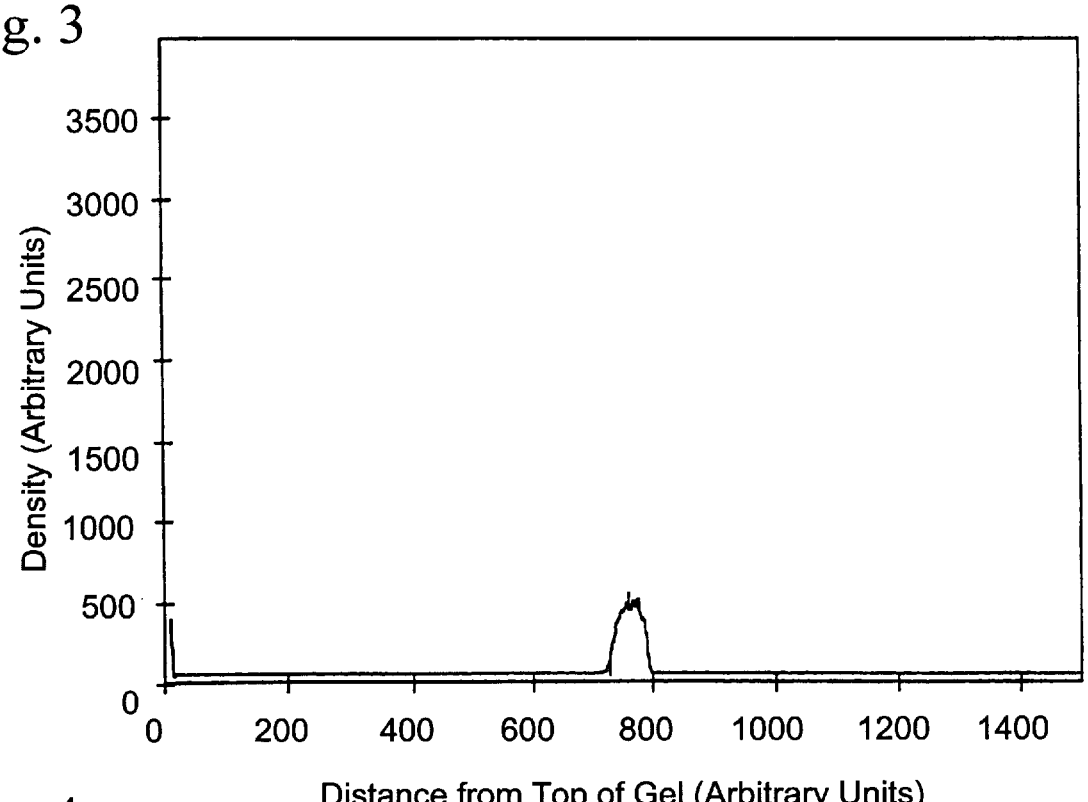
FIG. 3 is a densitometric scan of an immunoblot of an assay for transformed Ah receptor/ARNT complex with anti-ARNT after size exclusion chromotagraphy of a test sample without a dioxin-like compound.
Figure 4:
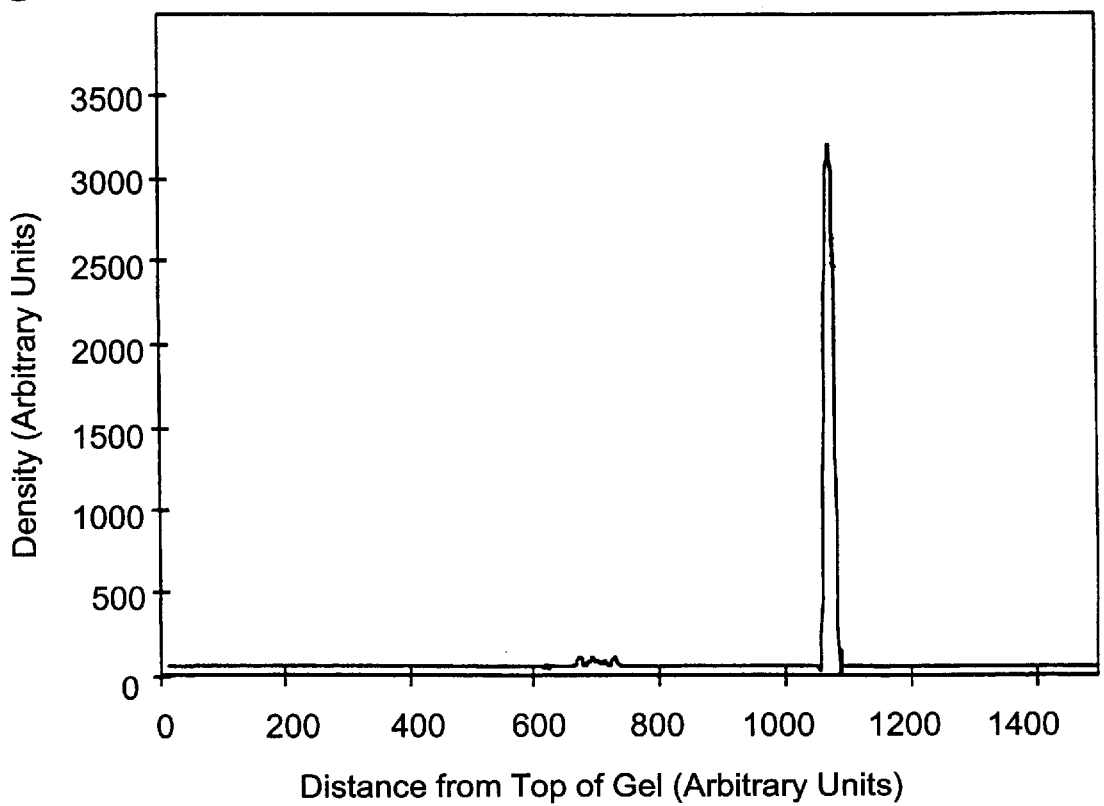
FIG. 4 is a densitometric scan of an immunoblot of an assay for transformed Ah receptor/ARNT complex with anti-ARNT after size exclusion chromotagraphy of a test sample with a dioxin-like compound.

FIG. 3 is a densitometric scam of an immunoblot of fraction 5 sample C. FIG. 4 is a densitometric scan of an immunoblot of fraction 5 sample D. Fraction 5 of sample D showed a band at the size of rabbit IgG light chain (circa 25 kD) that was absent in fraction 5 of sample C. These results show that this protein migrates as a high molecular species in a TCDD dependent manner consistent with it being the anti-ARNT part of the transformed DRE/AhR/ARNT/anti-ARNT complex. Thus size exclusion chromatography can resolve the TCDD-dependent DRE/AhR/ARNT/anti-ARNT complex from interfering substances which allows the complex to be detected.

EXAMPLE 6

Size-exclusion of biotin-DRE/AhR/ARNT/anti-ARNT complex followed by capture on neutravidin ELISA plates and detection with anti-rabbit/alkaline phosphatase conjugate.

Diethanolamine buffer was prepared by dissolving 0.4 g Magnesium chloride hexahydrate, 0.8 g sodium azide, 338 mL diethanolamine in 2.5 L deionized water, adjusting pH to 9.8 with concentrated HCl, and adjusting volume to 4 liters.

PNPP stock was prepared fresh by dissoving two 15 mg tablets of para-nitro phenyl phosphate (Sigma, St. Louis, Mo.) in 20 mL diethanolamine buffer.

The same size exclusion column operating conditions were used as described above, except the DRE used was B-ERD oligo (SEQ. ID. #3) and DRE-D oligo (SEQ. ID #1)hybridized as described in methods. Cytosol was prepared as described above and was dosed with 1:1000 v/v DMSO (−) or 1:1000 v/v 10 uM 2,3,7,8-tetrachlorodibenzo-p-dioxin in DMSO (+).

Assay tubes were set up as follows:

| Sample | Cytosol | DRE | anti-ARNT |
|--------|---------|-----------|-----------|
| DMSO | (−) 800 uL | 1.25 nmol | 2 uL |
| TCDD | (+) 800 uL | 1.25 nmol | 2 uL |

Samples were incubated for 2 hours at room temperature as described above to achieve transformation/binding events then put on ice. Each sample was loaded onto SEC and chromatography developed at a flow rate of 0.5 ml/min. Eluant fractions were collected at 15 second intervals between 1.5–13.5 min post injection. Fractions, 48 total for each sample, were collected directly into a 96 well ELISA plate containing bound neutravidin (Pierce, Rockford, Ill.). The plate was incubated 2 hours, washed 3 times with 300 uL per well PBS plus 0.02% Tween 20, incubated 1 hour with 200 uL per well 1:1000 anti-rabbit/alkaline phosphatase conjugate in PBS plus 0.02% Tween 20 and 0.1% bovine serum albumin, washed 3 times with 300 uL per well PBS plus Tween 20 and developed 2 hours with 200 uL per well PnPP stock, and the optical density read at 405 nm in an ELISA spectrophotometer.

Figure 5:
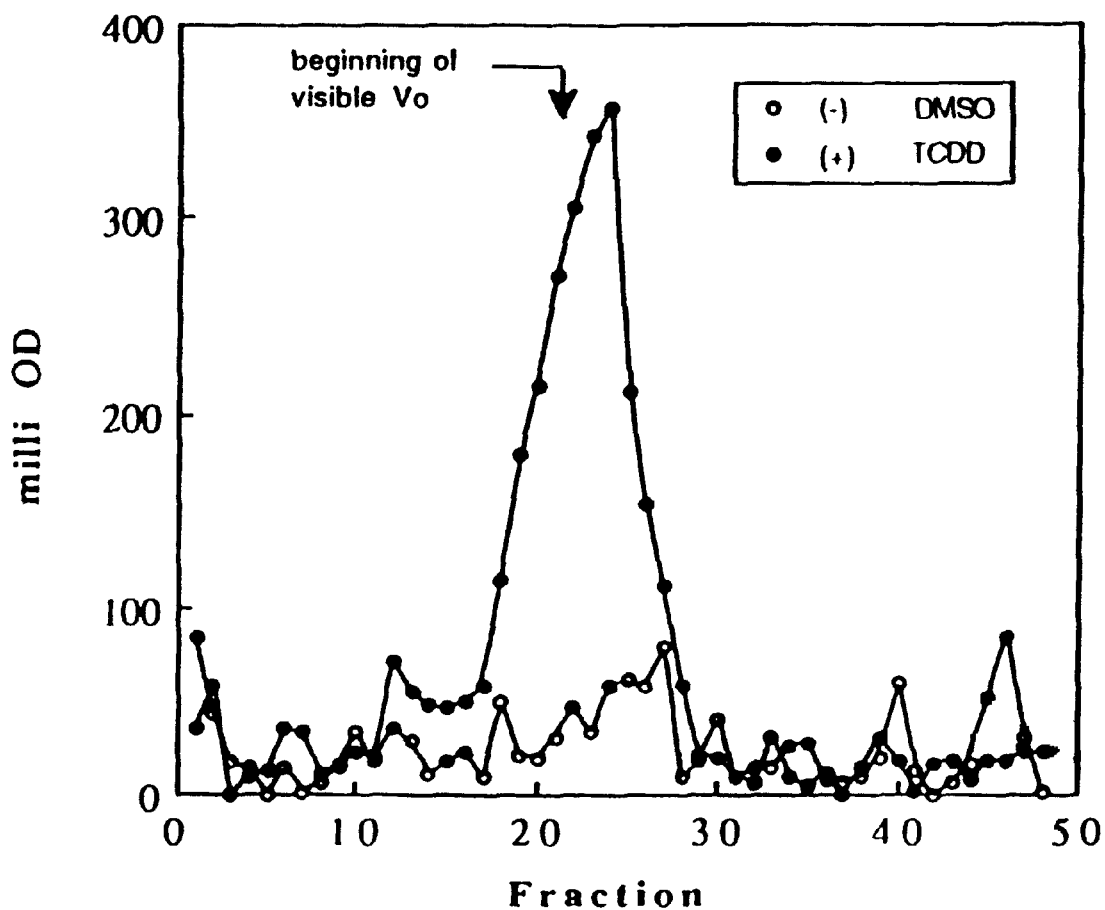
FIG. 5 is a graph showing a TCDD-dependent peak can be resolved through size exclusion chromotagraphy.

The results are shown graphically in FIG. 5. A TCDD-dependent peak across fractions 18–28 can be seen which corresponds to the void volume area of the gel. Thus this complex is large. Since it specifically binds to the neutravidin plate it must contain B-DRE. Since it is detected with anti-rabbit/alkaline phosphatase conjugate it must also contain anti-ARNT. This shows that a sandwich ELISA of AhR is possible and that size exclusion chromotagraphy works to seperation transformed AhR/ARNT complex from non-transformed AhR. Of the various formats for the transformed AhR/ARNT immuno assay, this technique is especially appealling because it is quick, accurate and inexpensive.

EXAMPLE 7

Detection of TCDD by detection of transformed Ah receptor/ARNT complex using a sandwich ELISA Method Working dilution of anti-ARNT was diluted (1:200, 50 uL in 10 mL) in PBS plus 0.02% tween 20 plus 0.1% bovine serum albumin. Working dilution of anti-Rabbit/alkaline phosphatase (Sigma, St. Louis, Mo.) was prepared by diluting 20 uL into 20 mL PBS plus 0.02% tween 20 plus 0.1% bovine serum albumin to make a 1:1000 dilution. Diethanolamine buffer was prepared by dissolving 0.4 g Magnesium chloride hexahydrate, 0.8 g sodium azide, 338 mL diethanolamine in 2.5 L deionized water, adjusting pH to 9.8 with concentrated HCl, and adjusting volume to 4 liters. PnPP stock was prepared fresh by dissoving two 15 mg tablets of para-nitro phenyl phosphate (Sigma, St. Louis, Mo.) in 20 mL diethanolamine buffer.

B-DRE (sequence ID 2) and DRE-D (sequence ID 1) were hybridized as described above. Cytosol was prepared as described above. Thirty five mL of cytosol was thawed and pooled. The cytosol was divided into two 17 mL aliquots and treated with either 17 uL DMSO, sample labled (−) or 17 uL 10 uM TCDD in DMSO with the sample labled (+). DMSO-treated cytosol (1700 uL) was mixed with 10.6 uL hybridized DRE (sample labeled B-). TCDD-treated cytosol (1700 uL) was mixed with 10.6 uL hybridized DRE (sample labeled B+).

A neutravidin-coated 96 well ELISA plate (Pierce), with the standard 12×8 well matrix, labeled 1–12 horizontally and A-H vertically, was warmed to room temperature. DMSO treated cytosol (−) was put in wells A2-A12 x D2-D12 at 200 uL per well. TCDD treated cytosol (+) was put in wells E2-E12 x H2-H12 at 200 uL per well. Untreated Cytosol plus DRE sample (B-), 400 uL per well, was put in wells A1-D1. Treated Cytosol sample plus DRE (13+), 400 uL per well, was put in wells D1-H1. The Untreated cytosol plus DRE sample (B-) and treated cytosol sample plus DRE (B+) were then serially diluted 1:1 across the plate, resulting in a serial dilution of DRE in either 200 uL treated or 200 uL untreated cytosol. The last column (A12H12) contained 400 uL, so 200 uL of that was discarded. Highest dilution of DRE in column A1-H1 was arbitrarily called 1, with the other dilutions labeled 0.5, 0.25 . . . 0.0005 respectively.

The ELISA plate was incubated with gentle rocking for 2 hours to allow the transformaton of Ah receptor, binding of Ah receptor with ARNT, and binding of the Ah receptor/ARNT complex to the biotinylated DRE, and binding of the biotinylated DRE to the neutravidin bound to the ELISA plate.

After 2 hours the plate was washed 3 times with 300 uL PBS plus 0.02% tween 20 and 400 uL of the working dilution of anti-ARNT added to rows A1-A12 and E1-E12 of the ELISA plate. 200 uL of PBS plus 0.02% tween 20 plus 0.1% bovine serum albumin was added to the remaining wells. Row A1-A12 was serially (1:1) diluted through rows B-D. Row E was serially diluted through rows F-H. This resulted in an anti-ARNT dilution of 1:200 in rows A,E; 1:400 in rows B,F; 1:800 in rows C,G; and 1:1600 in rows D,H. The plate was again incubated with gentle rocking at room temperature for 2 hours. After 2 hours the plate was washed as before and working dilution (1:1000) of anti-rabbit/alkaline phosphatase conjugate was added to all wells. The plate was incubated for a further 1 hour at room temperature with gentle rocking and then washed as before. PnPP stock was added to each well (200 uL) and the plate was incubated for 1 hour, at which time it was read at 405 nm in an ELISA plate reader and milli O.D. recorded.

Results

| anti-ARNT dilution | DRE dilutions | | | | | | | | | | | |
|---|---|---|---|---|---|---|---|---|---|---|---|---|
| | 1 | 0.5 | 0.25 | 0.125 | 0.063 | 0.031 | 0.016 | 0.008 | 0.004 | 0.002 | 1E-03 | 5E-04 |
| 0.005 | 889 | 783 | 763 | 771 | 838 | 851 | 936 | 986 | 1009 | 1018 | 1043 | 1131 |
| 0.0025 | 585 | 528 | 503 | 513 | 549 | 573 | 601 | 640 | 621 | 639 | 648 | 710 |
| 0.00125 | 457 | 423 | 407 | 409 | 417 | 443 | 438 | 459 | 453 | 460 | 474 | 553 |
| 0.000625 | 379 | 328 | 335 | 317 | 340 | 348 | 351 | 376 | 356 | 363 | 390 | 497 |
| 0.005 | 771 | 765 | 777 | 963 | 1202 | 1706 | 2122 | 2558 | 2029 | 1524 | 1070 | 1191 |
| 0.0025 | 585 | 544 | 532 | 608 | 804 | 1125 | 1486 | 1682 | 1281 | 922 | 680 | 722 |
| 0.00125 | 387 | 393 | 406 | 487 | 537 | 767 | 916 | 1070 | 932 | 595 | 484 | 498 |
| 0.000625 | 408 | 393 | 392 | 411 | 480 | 562 | 639 | 726 | 595 | 463 | 442 | 480 |

Conclusions

This example shows that TCDD gives a differential response by detection of transformed Ah receptor/ARNT complex using a sandwich ELISA. The optimal dilution of DRE was 1/32 of the highest dilution, which corresponds to a final dilution of 0.25 nmol/uL hybridized DRE x 10.6 uL DRE/1700 uL cytosol or 31.2 pmol per well. The optimal dilution of anti-ARNT was 1:400 of the 110 ug/mL stock, which corresponds to a final dilution of 0.275 ug per mL. The assay was also sensitive enough that only 200 uL of cytosol showed a response.

EXAMPLE 8

Optimization of Salt Concentration in Ah-ELISA Assay

Method

The reagents and ELISA plate were prepared as described in Example 7, except the anti-Rabbit/alkaline phosphatase (Sigma, St. Louis, Mo.) was prepared to make a 1:4000 dilution. The final DRE dilution was 31.2 pmol per well. The final dilution of anti-ARNT was 0.275 ug per mL. The DRE was 1/32 of the highest dilution, which corresponds to a final dilution of 0.25 nmol/uL hybridized DRE x 10.6 uL DRE/1700 uL cytosol or 31.2 pmol per well. All other concentrations were the same. All assays were run at approximately 30° C.

The salt concentration during cytosol incubation was varied from 150 mM to 255 mM NaCl at 15 mM increments with a 0 mM NaCl control for with either DMSO or TCDD to determine the effect of salt concentration on background detection. Thus, the assay was run on samples with DMSO (−) or TCDD (+) added at the concentrations taught in Example 7.

Results

| SALT | 0 | 150 | 165 | 180 | 195 | 210 | 225 | 240 | 255 | S9 |
|---|---|---|---|---|---|---|---|---|---|---|
| (−) | 354.6 | 151.9 | 131.3 | 106.6 | 102.9 | 87.58 | 81.25 | 84.58 | 100.2 | 129.9 |
| (+) | 2233 | 2739 | 2756 | 2767 | 2712 | 2303 | 1779 | 1418 | 1210 | 216.6 |
| DIFF | 1879 | 2587 | 2625 | 2661 | 2609 | 2215 | 1697 | 1333 | 1109 | 86.67 |
| RATIO | 6.298 | 18.03 | 21 | 25.96 | 26.35 | 26.29 | 21.89 | 16.76 | 12.07 | 1.667 |

Conclusions

This work showed that the best ratio of background to detection of TCDD was obtained at a salt concentration of 180–195 mM NaCl during cytosol incubation.

EXAMPLE 9

Further Optimization of Ah-ELISA Assay

Method

The reagents and ELISA plate were prepared as described in Example 8. The volume of cytosol, temperature of cytosol incubation and time of incubation were all varied independently. The test volume of cytosol was varied between 50 and 200 µl at 50 µl increments. The assay was run at 22° C., 30° C. and 35° C. during cytosol incubation. The assay was with a cytosol incubation varying between 30 and 120 minutes at 30 minute increments.

Results

| vol (uL) | 50 | 100 | 150 | 200 | 200 | 200 | 200 | 200 | 200 | 200 |
|---|---|---|---|---|---|---|---|---|---|---|
| time(min) | 120 | 120 | 120 | 120 | 30 | 60 | 90 | 120 | 120 | 30 |
| temp(c) | 30 | 30 | 30 | 30 | 30 | 30 | 30 | 22 | 35 | 38 |
| ave(−)-BG | 21.7 | 33 | 43 | 45 | 35 | 36.3 | 43 | 60.3 | 61 | 28 |
| ave(+)-BG | 1006 | 1463 | 1910 | 2369 | 394 | 1324 | 1882 | 1924 | 959 | 525 |
| difference | 984 | 1430 | 1867 | 2324 | 359 | 1288 | 1839 | 1863 | 898 | 497 |

Conclusions

The test improved as volume of cytosol and time of incubation increased. As a practical limitation 200 µl is the maximum volume of cytosol that can be used for the well implemented and incubating for any longer than 2 hours is impractical for the user. The optimal temperature was determined to be 30° C. This work merely confirmed that the initial conditions selected for each of these variables was optimal for the assay being tested.

EXAMPLE 10

Dose Response for the Ah-ELISA Assay Using a PnPP Detection

Method

The reagents and ELISA plate were prepared as described in Example 9 with the standard PNPP detection technique. The TCDD concentration was varied tested at 0, 0.016, 0.031, 0.063, 0.125, 0.25, 0.5, and 1.0 nM. After washing the plates PnPP stock was added to each well (200 uL) and the plate was incubated for 1 hour (actually 58 minutes for data shown below), at which time it was read at 405 nM in an ELISA plate reader and milli O.D. recorded.

Results

| nM TCDD | Average Optical Density | Standard Deviation |
|---|---|---|
| 1 | 2.155 | 0.091 |
| 0.5 | 1.409 | 0.07 |
| 0.25 | 0.804 | 0.035 |
| 0.125 | 0.527 | 0.014 |
| 0.063 | 0.4 | 0.007 |
| 0.031 | 0.338 | 0.007 |
| 0.016 | 0.3 | 0.005 |
| 0 | 0.259 | 0.021 |

Conclusions

Figure 6:
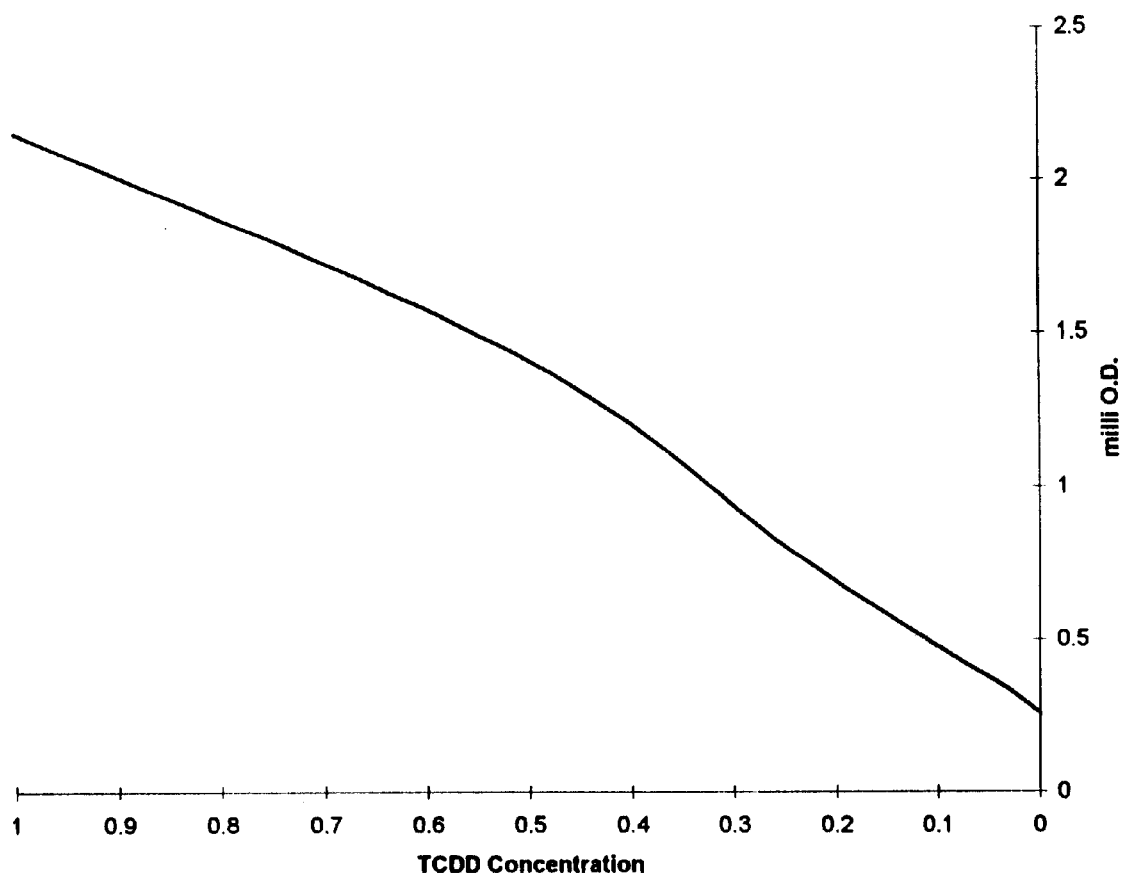
FIG. 6 shows the dose response curve for the Ah-ELISA assay using a PnPP detection system.

FIG. 6 shows the dose response curve for the Ah-ELISA assay using a PnPP detection system. The $EC_{50}$ was calculated to be 0.5 nm or about 80 parts per trillion. The limit of quantitation was calculated to be about 0.016 nm or about 5 parts per trillion. The limit of detection was also calculated to be about 0.016 nm or about 5 parts per trillion. This work proves that the Ah-ELISA assay in an extremely sensitive system that can detect concentrations well below other detection systems.

EXAMPLE 11

Dose Response for the Ah-ELISA Assay Using an Amplified Detection System

Method

The reagents and ELISA plate were prepared as described in Example 9 with an amplified detection system. The TCDD concentration was varied tested at 0, 0.016, 0.031, 0.063, 0.125, 0.25, 0.5, 1.0, 2.0, and 4.0 nM.

The amplified detection system used was the alkaline phosphatase/NADP system published by Johannson et al. (J IMM Meth 87: 7–11, 1986). This system is sold as a kit under the trademark Ampak™ by DAKO.

2x enzyme stock was made by dissolving 8 mg alcohol dehydrogenase, 1.4 mg Diaphorase, 133 mg bovine serum albumin in 40 ml AMP buffer (2.3 g 85% HPLC grade phosphoric acid in a total volume of 960 ml water, pH adjusted to 7.2 with 6N NaOH, and 40 ml of ethanol was added to make 1 L). 2x INT stock was made by dissolving 50 mg INT Violet dye in 50 mL AMP buffer.

After washing the plates, 100 µl of NADP stock (0.837 mg in 10 ml of AP buffer (diethanolamine 50 mM, 1 mM MgCl$_2$, 0.1 mM ZnCl$_2$, 15 mM NaN$_3$, pH 9.5)) was added and allowed to incubate at room temperature for 30 minutes. Sensitivity can be increased by increasing amount of NADP or time of incubation. The 2x enzyme stock and 2x INT stock were mixed and 200 μl of the mixture was added per well. The OD was read at 490 nM (usually read at 1 minute intervals for up to 30 minutes). The results are shown below at 28 minutes.

Results

| nM TCDD | Average Optical Density | Standard Deviation |
|---------|-------------------------|--------------------|
| 4       | 1.844                   | 0.093              |
| 2       | 1.803                   | 0.095              |
| 1       | 1.421                   | 0.056              |
| 0.5     | 1.036                   | 0.021              |
| 0.25    | 0.675                   | 0.028              |
| 0.125   | 0.414                   | 0.005              |
| 0.063   | 0.293                   | 0.006              |
| 0.031   | 0.228                   | 0.004              |
| 0.016   | 0.203                   | 0.002              |
| 0       | 0.159                   | 0.004              |

Conclusions

Figure 7:
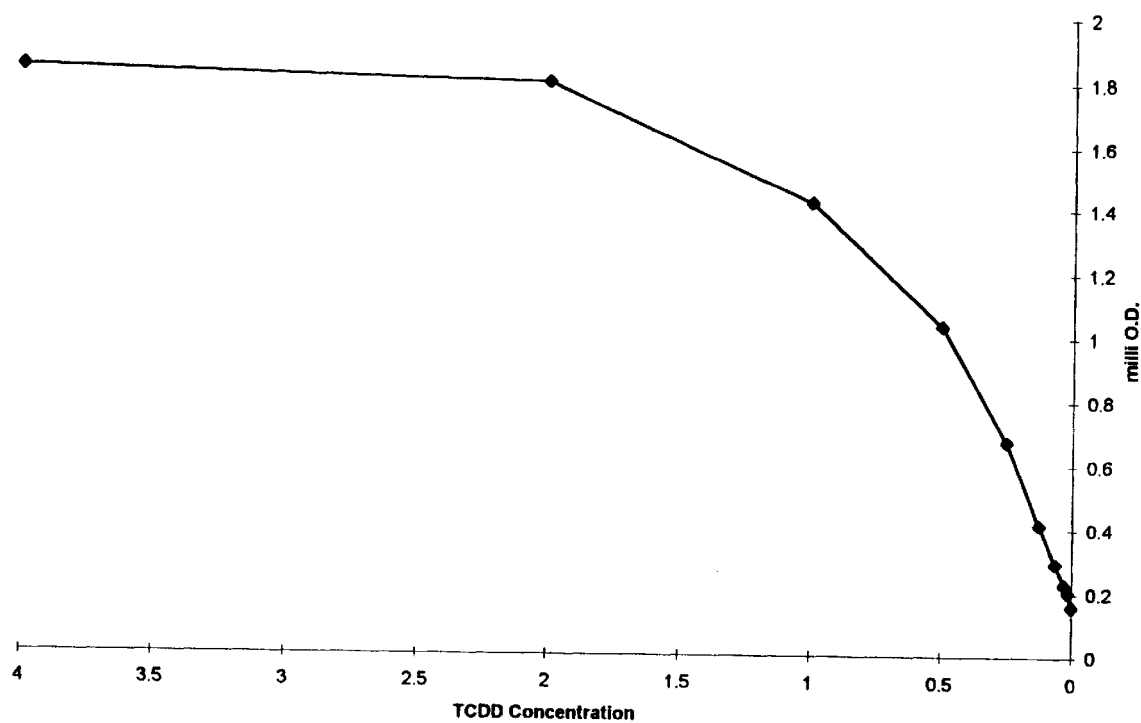
FIG. 7 shows the dose response curve for the Ah-ELISA assay using an amplified detection system.

FIG. 7 shows the dose response curve for the Ah-ELISA assay using an amplified detection system. The EC$_{50}$ was calculated to be 0.5 nm or about 80 parts per trillion. The limit of quantitation was calculated to be about 0.016 nm or about 5 parts per trillion which equals 1 pg/well. The limit of detection was also calculated to be about 0.28 parts per trillion which equals 0.056 pg/well. This work proves that the Ah-ELISA assay in an extremely sensitive system that can be improved by standard amplification systems.

Accordingly, it is to be understood that the embodiments of the invention herein described are merely illustrative of the application of the principles of the invention. Reference herein to details of the illustrated embodiments are not intended to limit the scope of the claims, which themselves recite those features regarded as essential to the invention.

What is claimed is:

1. A method of detecting dioxin-like compounds wherein said compounds are selected from the group of compounds consisting of polychlorinated dibenzodioxins, polychlorinated dibenzofurans, polychlorinated biphenyls, and structural analogues thereof which exhibit biological activity characteristic of polychlorinated dibenzodioxins, polychlorinated dibenzofurans, polychlorinated biphenyls, wherein said method comprises:

a) selecting a test sample;
b) providing assay reagents including:
1. an inactive Ah receptor in a form capable of binding to said dioxin-like compounds and being transformed thereby to an active form that forms a complex with ARNT and binds a dioxin responsive element; and
2. a quantity of ARNT sufficient to optimize said inactive Ah receptor transformation of previous step b)1 in response to said dioxin-like compounds;
c) contacting said test sample with said assay reagents under conditions effective to bind said dioxin-like compounds to said Ah receptor and allow transformation of said Ah receptor to an active form that forms a complex with ARNT; and
d) detecting the presence of said complex containing the transformed Ah receptor and said ARNT with an antibody having within it a region capable of detecting and binding said ARNT protein present in said complex, and thereby detecting the presence of said dioxin-like compound.

2. The method of claim 1 wherein the presence of said complex containing the transformed Ah receptor and said ARNT is detected with an antibody with a region capable of binding to said ARNT when said ARNT is part of said complex.

3. A method of detecting dioxin-like compounds wherein said compounds are selected from the group of compounds consisting of: polychlorinated dibenzodioxins, polychlorinated dibenzofurans, polychlorinated biphenyls, and structural analogues thereof which exhibit biological activity characteristic of polychlorinated dibenzodioxins, polychlorinated dibenzofurans, polychlorinated biphenyls, wherein said method comprises:

a) selecting a test sample;
b) providing assay reagents including inactive Ah receptors for an assay in a form capable of binding to said dioxin-like compounds, and being transformed thereby into a active form capable of binding to said dioxin-like compounds and forming a complex with ARNT and binds a dioxin responsive element;
c) contacting said test sample with said assay reagents under conditions effective to bind said dioxin-like compounds to said Ah receptor and allow transformation of said Ah receptor to an active form that forms a complex with ARNT; and
d) detecting the presence of said complex containing the transformed Ah receptor and said ARNT with a antibody with a region capable of binding to said ARNT when the ARNT is part of said complex.

4. The method of claim 3 wherein said assay includes a quantity of ARNT sufficient to optimize said transformation of said inactive Ah receptor of claim 3 to an active state which forms a complex with ARNT.

5. The method of claim 1 wherein said assay is an enzyme linked immunosorbent assay for transformed Ah receptor.

6. The method of claim 3 wherein said assay is an enzyme linked immunosorbent assay for transformed Ah receptor.

7. The method of claim I wherein said complex is purified through an affinity gel chromatography column prior to detection of the transformed Ah receptor, wherein said dioxin responsive element is bound to said affinity gel chromatography column.

8. The method of claim 3 wherein said complex is purified through an affinity gel chromatography column prior to detection of the transformed Ah receptor, wherein said dioxin responsive element is bound to said affinity gel chromatography column.

9. The method of claim 1 wherein said complex is purified through a size exclusion chromatography column prior to detection of said complex.

10. The method of claim 3 wherein said complex is purified through a size exclusion chromatography column prior to detection of said complex.

11. A kit for detecting dioxin-like compounds wherein said compounds are selected from the group of compounds consisting of: polychlorinated dibenzodioxins, polychlorinated dibenzofurans, polychlorinated biphenyls, and structural analogues thereof which exhibit biological activity characteristic of polychlorinated dibenzodioxins, polychlorinated dibenzofurans, polychlorinated biphenyls, wherein said kit comprises providing assay reagents including:

a) an inactive Ah receptor in a form capable of binding to said dioxin-like compounds and being transformed to an active form that is capable of forming a complex with ARNT and binding a dioxin responsive element forming a complex;

b) a quantity of ARNT sufficient to optimize said inactive Ah receptor transformation of previous a); and c) an antibody that is capable of detecting the presence of said complex containing the transformed Ah receptor.

12. The kit of claim 11 wherein said means for detecting the presence of said complex is an antibody with a region capable of binding to said ARNT when associated with said complex.

13. The kit of claim 11 further comprising an affinity gel chromatography column, wherein said dioxin responsive element is bound to said column.

14. The kit of claim 11 further comprising a size exclusion chromatography column.

* * * * *

SEQUENCE LISTING

<160> NUMBER OF SEQ ID NOS: 5

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence:DRE-D
      oligonucleotide

<400> SEQUENCE: 1
gatccggagt tgcgtgagaa gagcca                                        26

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence:ERD-D
      oligonucleotide

<400> SEQUENCE: 2
tggctcttct cacgcaactc cggatc                                        26

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence:B-ERD
      oligonucleotide with biotin at 5' end

<400> SEQUENCE: 3
tggctcttct cacgcaactc cggatc                                        26

<210> SEQ ID NO 4
<211> LENGTH: 26
<212> TYPE: DNA
<213> ORGANISM: Artificial Sequence
<220> FEATURE:

-continued

```
<223> OTHER INFORMATION: Description of Artificial Sequence:F-ERD
      oligonucleotide with fluorescein at 5' end

<400> SEQUENCE: 4
tggctcttct cacgcaactc cggatc                                           26

<210> SEQ ID NO 5
<211> LENGTH: 22
<212> TYPE: PRT
<213> ORGANISM: Artificial Sequence
<220> FEATURE:
<223> OTHER INFORMATION: Description of Artificial Sequence:Ah Receptor
      synthetic antigen
<220> FEATURE:
<221> NAME/KEY: MOD_RES
<222> LOCATION: (2)
<223> OTHER INFORMATION: Nle

<400> SEQUENCE: 5

Cys Xaa Arg Lys Arg Arg Lys Pro Val Gly Lys Thr Val Lys Pro Ile
 1               5                  10                  15

Pro Ala Gln Gly Ile Lys
            20
```